(12) United States Patent
De Canniere et al.

(10) Patent No.: US 7,951,167 B2
(45) Date of Patent: May 31, 2011

(54) FLUIDTIGHT PUNCTURING AND OCCLUSION DEVICE FOR ANATOMICAL STRUCTURE

(75) Inventors: Bernard De Canniere, Brussels (BE); Michel Joie, Ernage (BE)

(73) Assignee: St. Jude Medical Systems AB, Uppsala (SE)

( * ) Notice: Subject to any disclaimer, the term of this patent is extended or adjusted under 35 U.S.C. 154(b) by 1179 days.

(21) Appl. No.: 11/144,024

(22) Filed: Jun. 1, 2005

(65) Prior Publication Data

US 2005/0288707 A1 Dec. 29, 2005

Related U.S. Application Data

(60) Provisional application No. 60/599,195, filed on Aug. 5, 2004.

(30) Foreign Application Priority Data

Jun. 28, 2004 (EP) .................................... 04102983

(51) Int. Cl.
*A61B 17/03* (2006.01)
*A61B 17/00* (2006.01)
(52) U.S. Cl. ...... 606/219; 606/139; 606/213; 227/175.1
(58) Field of Classification Search .................. 606/219; 623/23.72
See application file for complete search history.

(56) References Cited

U.S. PATENT DOCUMENTS

| 5,478,354 | A | * | 12/1995 | Tovey et al. | .................... | 606/219 |
| 5,695,504 | A | * | 12/1997 | Gifford et al. | ................ | 606/153 |
| 5,695,524 | A | * | 12/1997 | Kelley et al. | .................. | 606/219 |
| 5,785,713 | A | | 7/1998 | Jobe | | |
| 5,902,310 | A | * | 5/1999 | Foerster et al. | ............... | 606/142 |
| 6,149,667 | A | * | 11/2000 | Hovland et al. | ................ | 606/219 |
| 6,197,042 | B1 | * | 3/2001 | Ginn et al. | .................... | 606/213 |
| 6,277,140 | B2 | * | 8/2001 | Ginn et al. | .................... | 606/213 |
| 6,391,048 | B1 | * | 5/2002 | Ginn et al. | .................... | 606/213 |
| 6,632,238 | B2 | * | 10/2003 | Ginn et al. | .................... | 606/213 |
| 7,637,925 | B2 | * | 12/2009 | De Canniere et al. | ........ | 606/219 |
| 2002/0002386 | A1 | * | 1/2002 | Ginn et al. | .................... | 606/213 |
| 2002/0029064 | A1 | * | 3/2002 | Kanner et al. | ................ | 606/221 |
| 2002/0062130 | A1 | | 5/2002 | Jugenheimer et al. | | |
| 2002/0082641 | A1 | | 6/2002 | Aldrich et al. | | |
| 2004/0082906 | A1 | * | 4/2004 | Tallarida et al. | ................ | 604/43 |
| 2004/0249391 | A1 | * | 12/2004 | Cummins | ..................... | 606/139 |
| 2005/0055027 | A1 | * | 3/2005 | Yeung et al. | .................... | 606/75 |

FOREIGN PATENT DOCUMENTS

DE 41 10 123 A 10/1992

OTHER PUBLICATIONS

European Search Report "Rapport de Recherche Europeenne" EP 04 10 29830.

* cited by examiner

*Primary Examiner* — (Jackie) Tan-Uyen T Ho
*Assistant Examiner* — Mark Mashack
(74) *Attorney, Agent, or Firm* — Kilpatrick Townsend & Stockton LLP; Gerald T. Gray

(57) ABSTRACT

A combined device for plugging and fluidtight puncturing of a wall of a hollow organ, comprising a head bearing a surgical staple for the wall of the hollow organ, a fluidtight puncturing system comprising a puncturing device and a hollow channel, a keeping means for bringing the said staple from its open position to its closed position, a support connected to a traction member extending towards the distal part of the device. The device comprises an introducer capable of introducing the head of the device inside an organism. A staple particularly designed to fit this device is also describe.

12 Claims, 22 Drawing Sheets

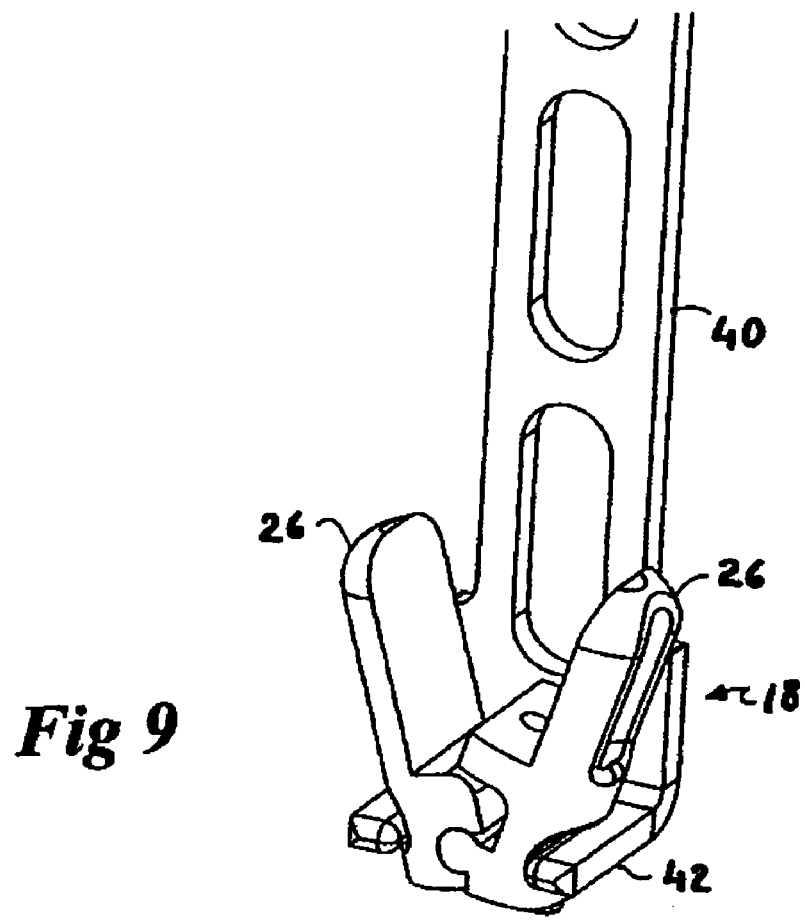
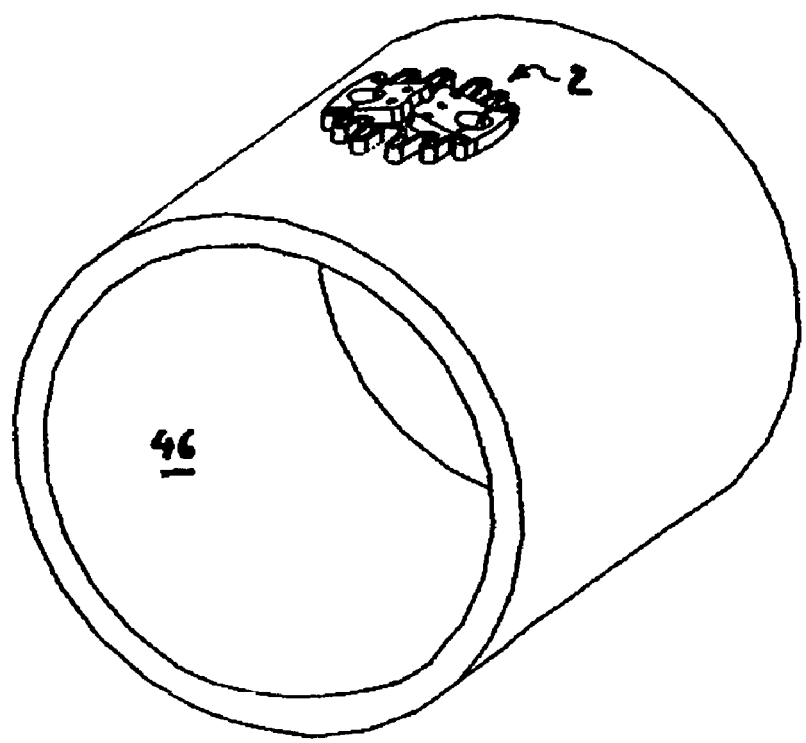
Fig 9

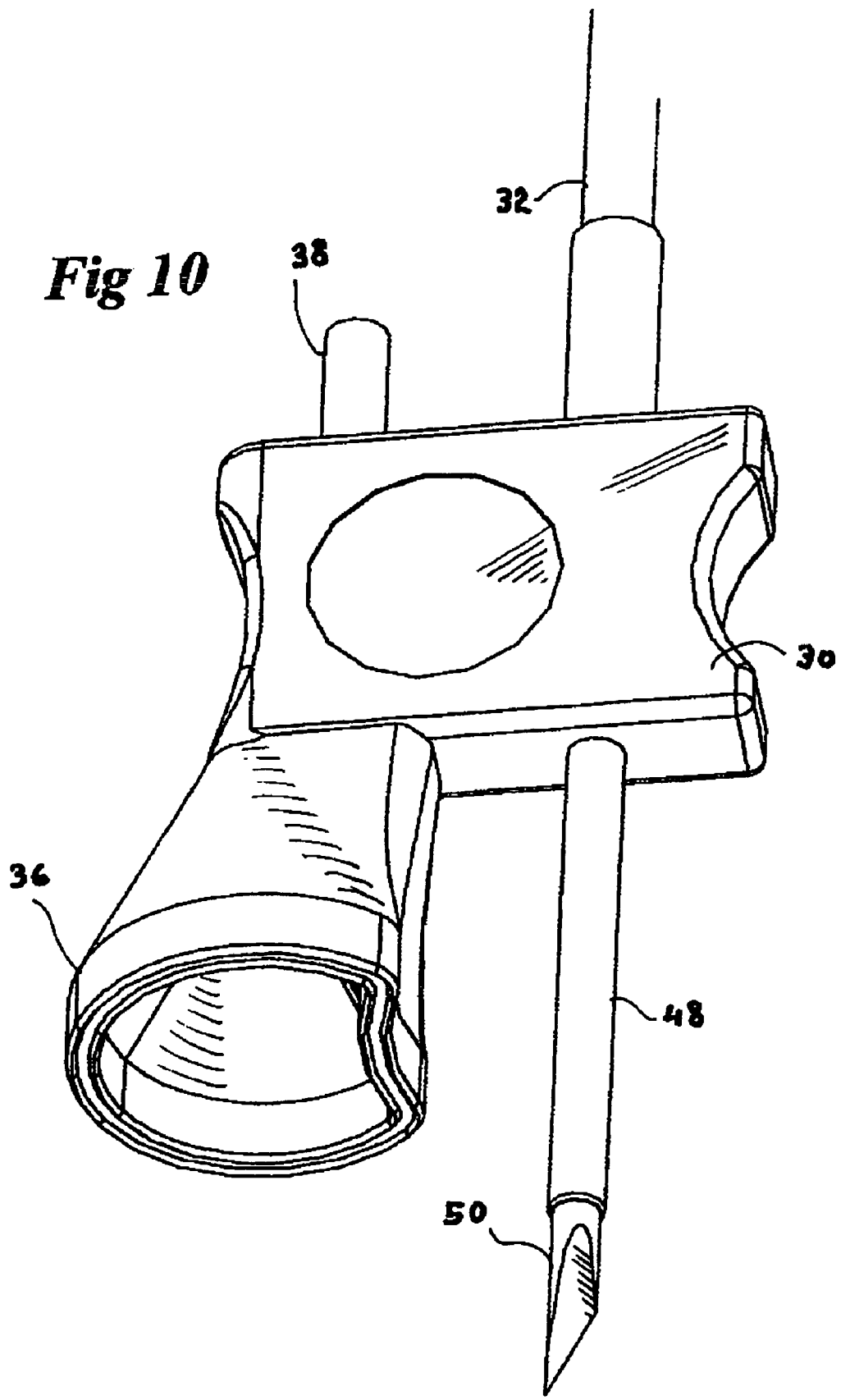

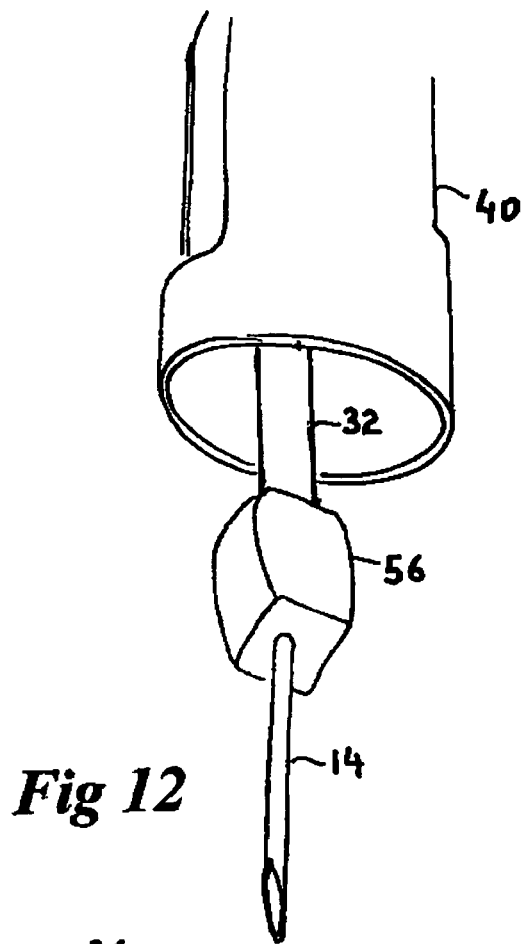
*Fig 12*
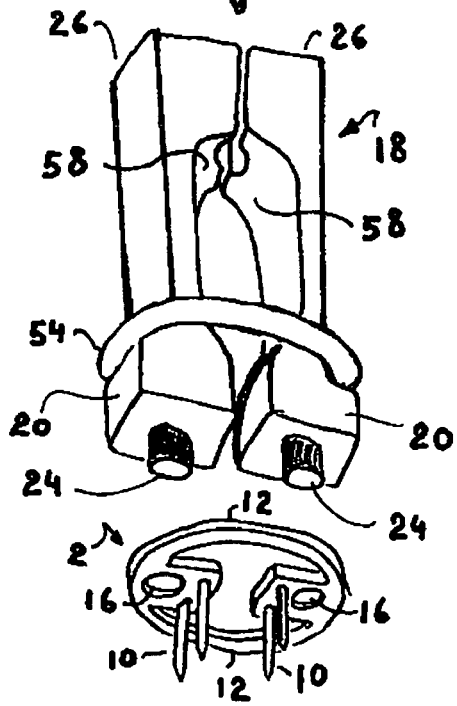
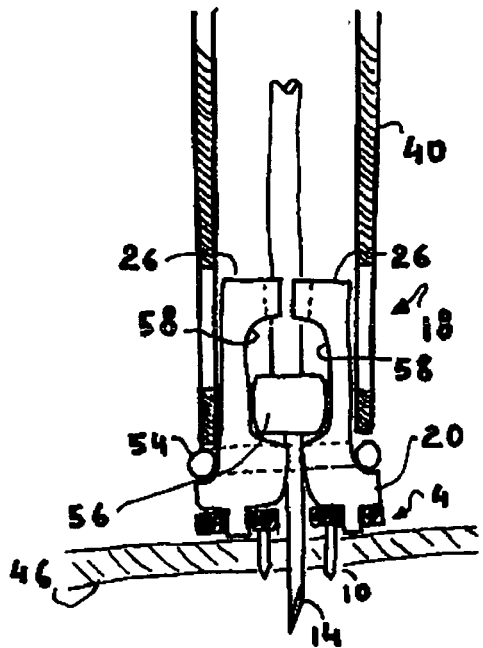
*Fig 13*
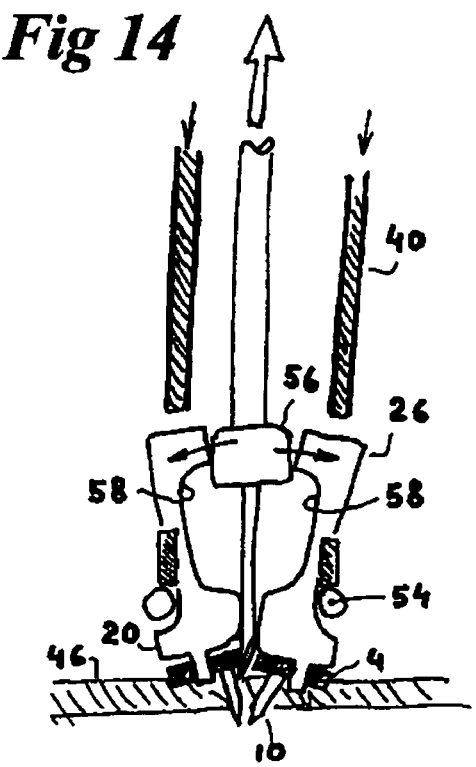
*Fig 14*

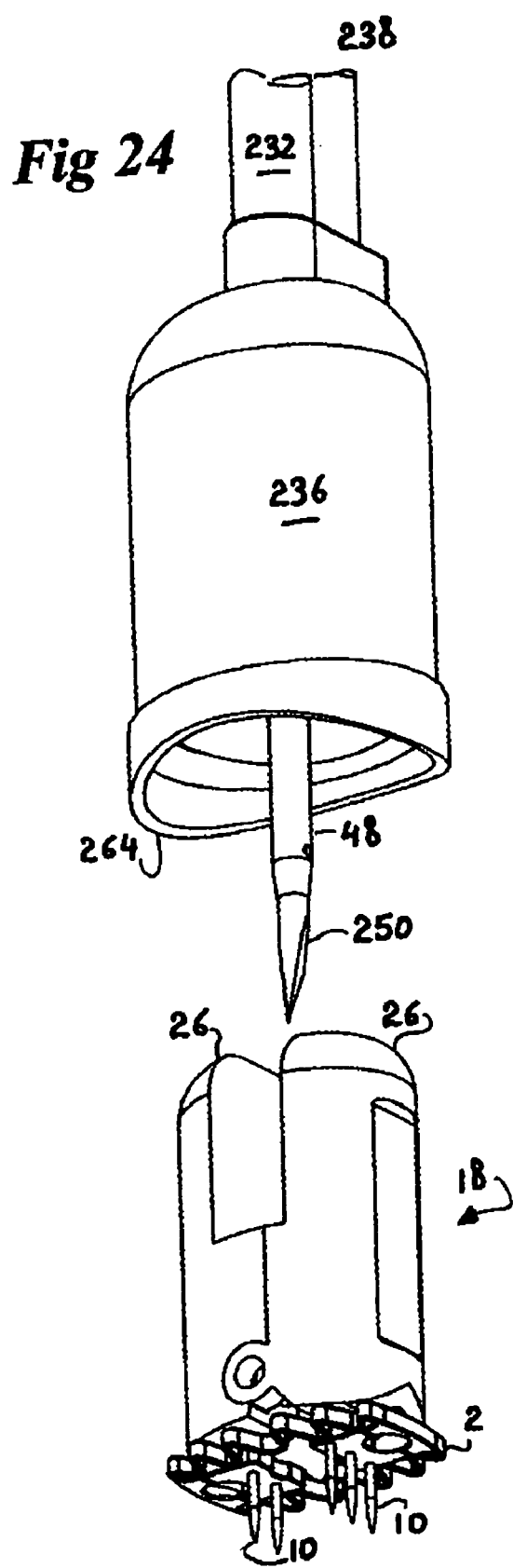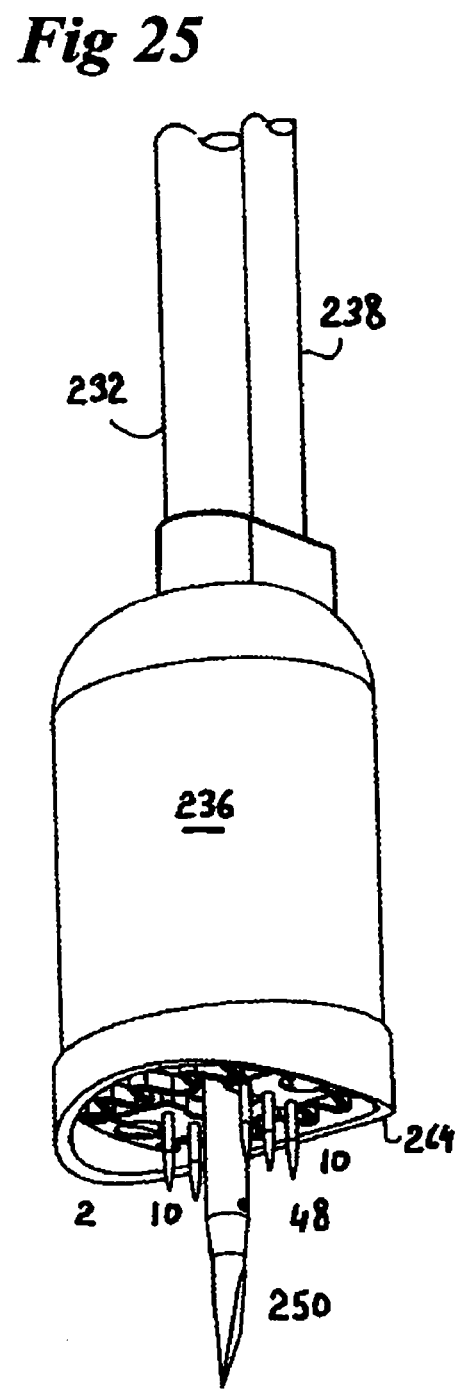

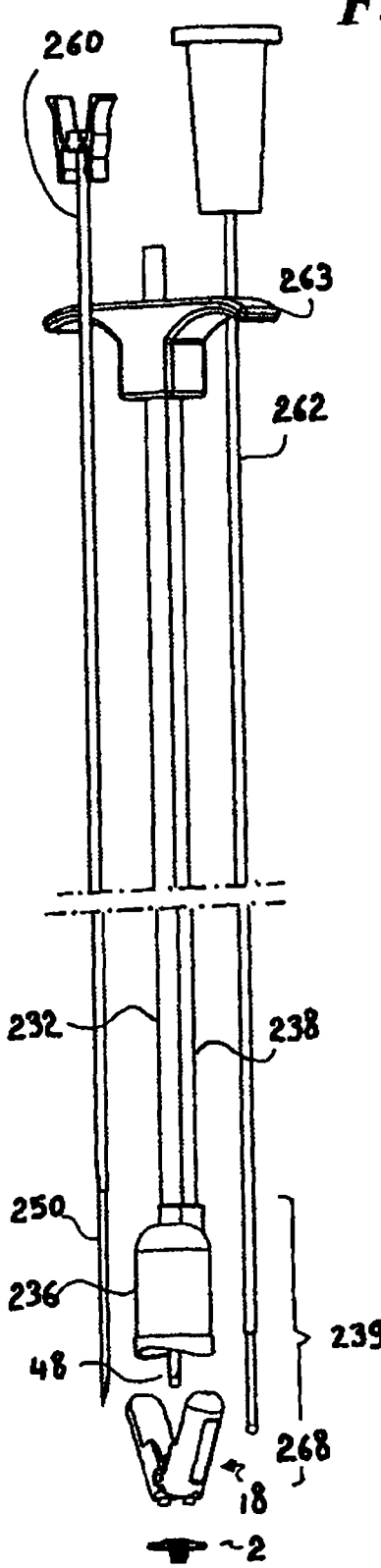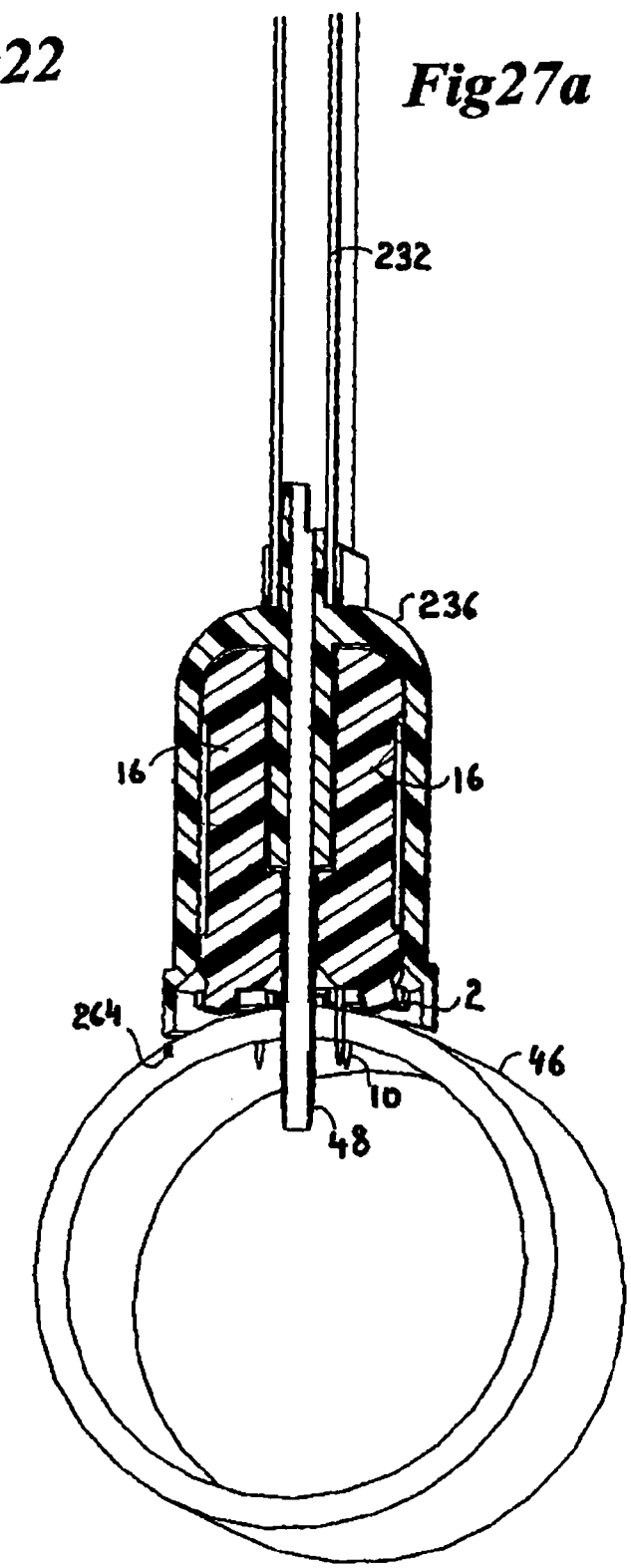

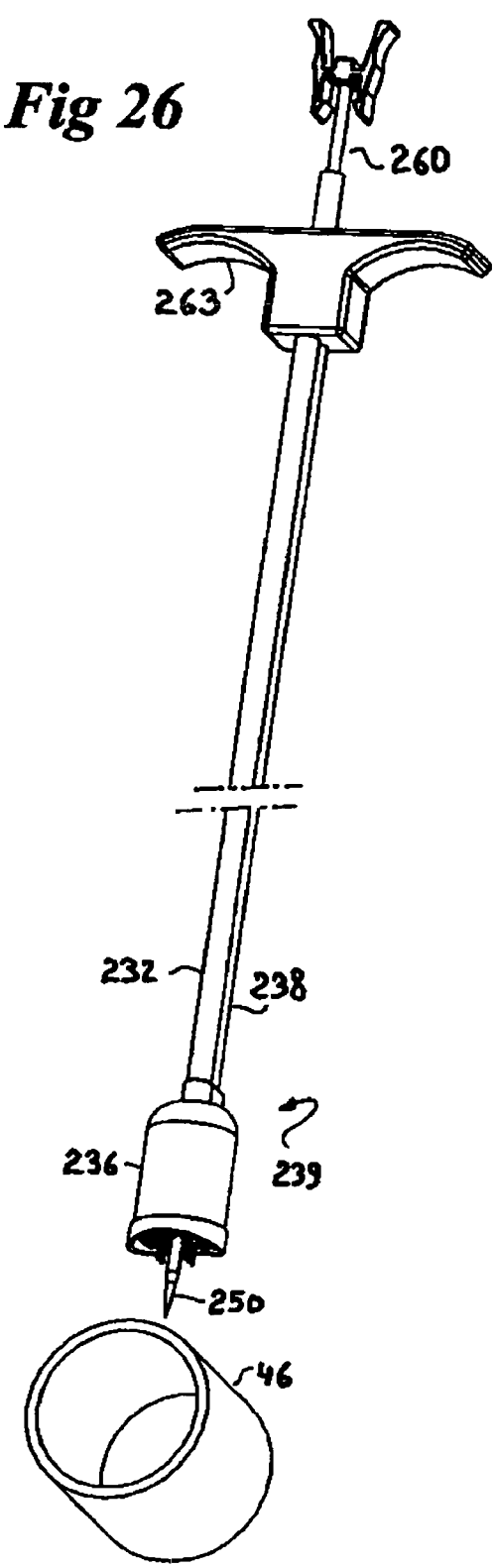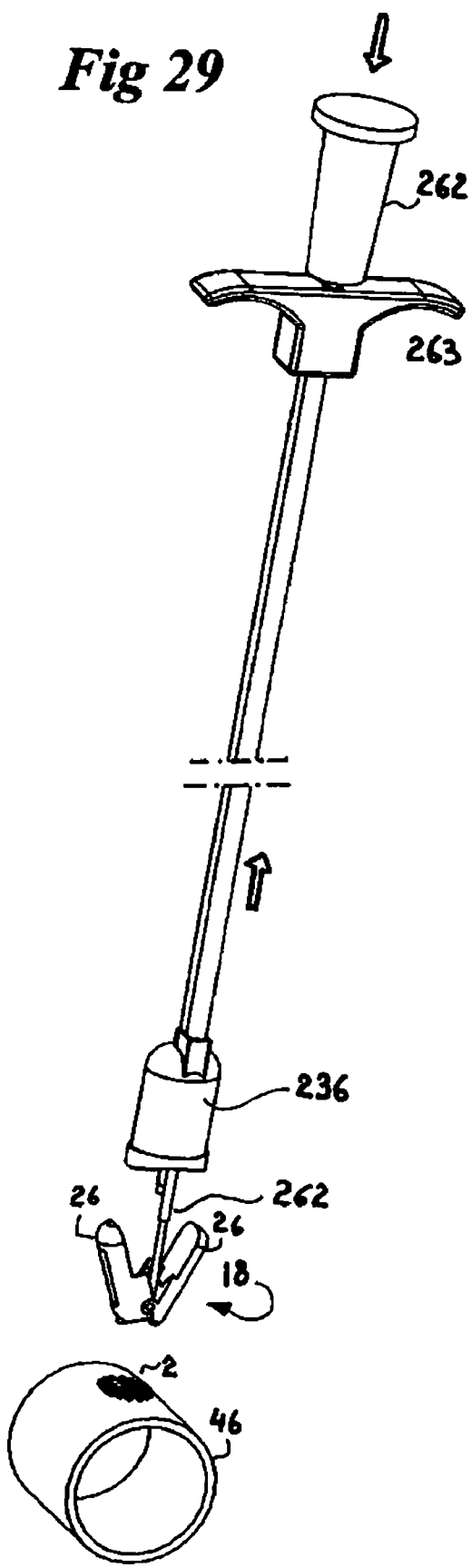

FLUIDTIGHT PUNCTURING AND OCCLUSION DEVICE FOR ANATOMICAL STRUCTURE

This application claims priority to U.S. provisional application Ser. No. 60/599,195 filed on Aug. 5, 2004.

The invention relates to an occlusion and puncturing device for both direct cannulation and puncturing in a hollow organ, and especially a vascular organ, but also in tracheas, intestines, etc. This device dispenses with the need for a surgical closure procedure when withdrawing the puncturing or cannulation system.

TECHNOLOGICAL BACKGROUND OF THE INVENTION

It is necessary, during an intervention on an artery, even as benign as a puncture or cannulation, to suture the wounded membrane, or even to affix a patch, as described in U.S. Pat. No. 3,988,782.

A still increasing use is made in medicine and in surgery of instruments which are introduced via the blood system. Several devices were thus developed for closing a blood vessel with a clip after a percutaneous puncturing.

US-2002/0082641 describes a method and a device for fitting a flat-shaped vascular clip corresponding roughly to the preamble of claim 1. However, this clip causes accentuated deformation (swelling) of the wall to be sutured and is relatively aggressive to install. Similar devices are known by US 2002/002386 and US 2002/082641. They describe in every case quite bulky percutaneous devices, which are put in place after the puncturing proper, the latter being performed with a cutting instrument like a lancet. These devices are generally used (like US 2002/002386) for introducing a catheter. Using such devices implies applying non-neglectible promptings on the surrounding tissues. After the removal of the device introduced in the blood stream, the fitting of the clip itself, even when made carefully, will shake the vessel as well as the surrounding tissues.

Heart surgery often requires the heart to be shut down so as to obtain a stationary and bloodless operating site allowing precise and delicate surgical handwork. This requires the use of extracorporeal circulation (ECC) so as to perfuse the systemic organs (brain, liver, kidneys, etc.) with oxygenated blood during the period when the heart is shut down.

To do this, the aorta has to be clamped, this operation usually consisting in closing off the vessel by an external clamp that is interposed between the arterial cannula allowing extracorporeal circulation and the orifice of the coronary arteries. This procedure isolates the coronary circulation from the blood flow provided by the ECC and therefore allows the heart to be shut down.

Injection of a solution into the network of coronary arteries (cardioplegia) protects the heart itself during the shutdown period.

Installing the extracorporeal circulation (ECC) system, the clamping and the cardioplegia conventionally require the sternum to be cut open and splayed (sternotomy). Sternotomy is firstly a destructive surgical procedure that frequently poses postoperative complications for the patient.

In recent years, alternative techniques have been developed for heart surgery with the aim of being less aggressive for the patient. The exclusion of sternotomy is one of these approaches. In this case, the invention is carried out by mini-incisions that allow endoscopic instruments to be introduced. The work is performed here on "free" (unbridled) organs, unlike the prior art devices as described above.

The object of the invention is to allow a connection to be made to an anatomical structure under pressure, making it possible to carry out a puncturing or cannulation step without spilling fluid, without having to close up the connection hole by suturing and while exerting as few mechanical constrains as possible on the organ.

Another object of the invention is to be able to close up a tear in a hollow organ, such as an artery, rapidly and lastingly.

Another object of the invention is the manufacturing of a device of such reduced dimensions that it can be used in minimally invasive surgery, i.a. with restricted operation access, via incisions measuring about 10 to 30 mm.

SUMMARY OF THE INVENTION

The subject of the invention is combined device for plugging and fluidthight puncturing of a wall of a hollow organ, comprising a proximal and a distal part, which comprises at its distal side a head bearing:

a surgical staple for the wall of the hollow organ, placed towards the distal part, said staple comprising a substantially flat back that can deform between a closed position of the staple and an open position of the staple, and at least two spaced-apart pins extending each along an axis, a free end of the pins converging when the back is in the closed position, the axes of the pins of the two rows tending to align parallel to each other when the staple is in open position the back of said staple being provided with a central opening a fluidthight puncturing system comprising a puncturing device and a hollow channel, the diameter of which corresponds to the central opening of the staple, said puncturing system being mounted on a support and connected to a fluid carrying conduit a keeping means for keeping the said staple in place, the said means being capable of bringing the said staple from its open position to its closed position;

a support connected to a traction member extending towards the distal part of the device, forming the head of the device; and an introducer capable of introducing the head of the device inside an organism.

The advantage of the invention is that it allows connection, especially by puncturing or cannulation, to an artery under pressure, such as the aorta, without having to manipulate it in order to close up the puncture holes with a suture, as the latter procedure is potentially deleterious, having a propensity to trigger embolisms or tearing of the arterial tissue and haemorrhaging. In contrast, in the present case the various layers of the arterial wall are kept in place virtually in their initial relative positions, which results in rapid cicatrization without any degradation in the properties of the wall.

According to a first advantageous embodiment, the staple is elastically deformable. In this case, the means for keeping the said staple in place is a clamp provided with two jaws and with locking means, the free ends of the jaws being provided with grasping means capable of cooperating with the gripping points of the staple, locking means keeping the said staple in place on the jaws in an open position.

According to a second advantageous embodiment, the staple is plastically deformable. In this case the means for keeping the said staple in place is a clamp provided with two jaws and with locking means, the free ends of the jaws being provided with grasping means capable of cooperating with the gripping points of the staple, second locking means keeping the said staple in place on the jaws in the open position, the jaws of the said clamp being able to be actuated by second clenching means causing plastic deformation of the back of the staple.

The clamp has preferably two jaws.

The tip of the puncturing device is advantageously manufactured and placed in the puncturing system in such a manner that the pins of the staple are placed on opposite sides of an incision made in the wall of a hollow organ and on a substantially symmetrical way with respect to said incision.

Advantageously, the distal head of the device is detachable from the introducer. The use of a detachable introducer allows the use of flexible conduits, thereby clearing the operating area.

The closing of the staple is advantageously actuated by the removal of the support. It is thus impossible to actuate the device in error during an operation. At the worst, this removal "automatically" closes the wound.

The introducer includes preferably, at its proximal side, a member for unlocking the clamp, so releasing the staple. This arrangement has the advantage of requiring the operator to keep the device in place against the hollow organ when closing the staple, thus preventing the latter from being incorrectly positioned. This unlocking member can be chosen to be actuated manually, electrically or pneumatically.

In a preferred embodiment, the support for the hollow needle further supports a retention device, advantageously a sucker, which can be applied against the wall of the hollow organ and can keep the head of the device in place thereon, the said sucker being connected to a duct that can be connected to a source of negative pressure. The presence of such a retention means allows the operator, once the device is in place, to devote himself completely to handling the other surgical instruments.

According to an advantageous embodiment, the puncturing device, the staple and the staple retaining means are placed inside the sucker. No torsion couple is thus applied to the device, which enhances the holding in place of the cannula. The introducer is advantageously plastically deformable so as to be able to present the puncturing device at right angles to a wall lying at any angle.

According to a preferred embodiment, the puncturing device includes a trocar that can be inserted through a hollow conduit.

Another subject of the invention is a surgical staple for a surgical device as described above, comprising a substantially flat back that can deform between a closed position of the staple and an open position of the staple, and at least two spaced-apart pins wherein:

the back comprises two parts that are hinged with respect to each other;

the at least two pins are arranged in two rows on these two parts, substantially lying along axes perpendicular to a plane of each of the two parts in the closed position of the back a free end of the pins of the two rows converge;

when the back is in the open position, the axes of the pins of the two rows tend to align parallel to each other and/or the tips of the pins are separated by a gap larger than in the closed position;

said staple being provided with a central opening and with gripping points for keeping the staple in one position.

When the staple is in place, its back does not protrude from the wall of the hollow organ. An advantage of such a design is that this staple is less cumbersome, does not perturbate the various layers of the stapled tissues and may possibly be removed without damaging the tissues.

According to a first advantageous embodiment, the back is elastically deformable. In this case, the two parts are preferably joined together by springy joins.

According to a second advantageous embodiment, the back is plastically deformable.

BRIEF DESCRIPTION OF THE DRAWINGS

Other features and advantages of the invention will become apparent from the following description of particular embodiments of the invention, reference being made to the appended drawings in which:

FIGS. 3 to 9 relate more particularly to a device of the invention in the case of an elastically deformable staple;

FIG. 3 is a perspective view on another scale of the clamp of the combined puncturing device according to the invention;

FIG. 4 is a perspective view of the clamp of FIG. 3 in the closed position;

FIG. 5 is an exploded view of the various constituents of the combined puncturing device according to the invention;

FIG. 6 is a perspective view of the head of the combined device at the moment of its application to an artery;

FIG. 7 is a more detailed perspective view of the head of the device after it has been applied to an artery;

FIG. 8 is a detailed perspective view of the release of the staple according to the invention;

FIG. 9 is a perspective view of the removal of the head of the device after the staple has been fitted;

FIG. 10 is a perspective view of another embodiment of the device according to the invention;

FIGS. 12 to 14 relate more particularly to an embodiment of the device according to the invention provided with a plastically deformable staple;

FIG. 12 is an exploded view of the head of a device provided with a plastically deformable staple;

FIGS. 13 to 14 are schematic perspective views of the two steps of fitting the staple using the device of FIG. 12;

FIGS. 22 to 28 are perspective views of still another embodiment of the introducer and of the placement device of the staple;

FIG. 22 is an exploded view of this embodiment;

FIG. 23 is a more detailed view of the embodiment of FIG. 22;

FIGS. 24 and 25 are perspective views of the embodiment of FIG. 22;

FIG. 26 is a sketch of the putting in place of the embodiment of FIG. 22;

FIG. 27a is a sectional view of the putting in place of the embodiment of FIG. 22;

FIG. 28 is a detailed perspective view of the putting in place of staple with the embodiment of FIG. 22;

FIG. 29 is a general perspective view of a step following the one described at FIG. 22;

DETAILED DESCRIPTION OF THE DRAWINGS

Figure 1:
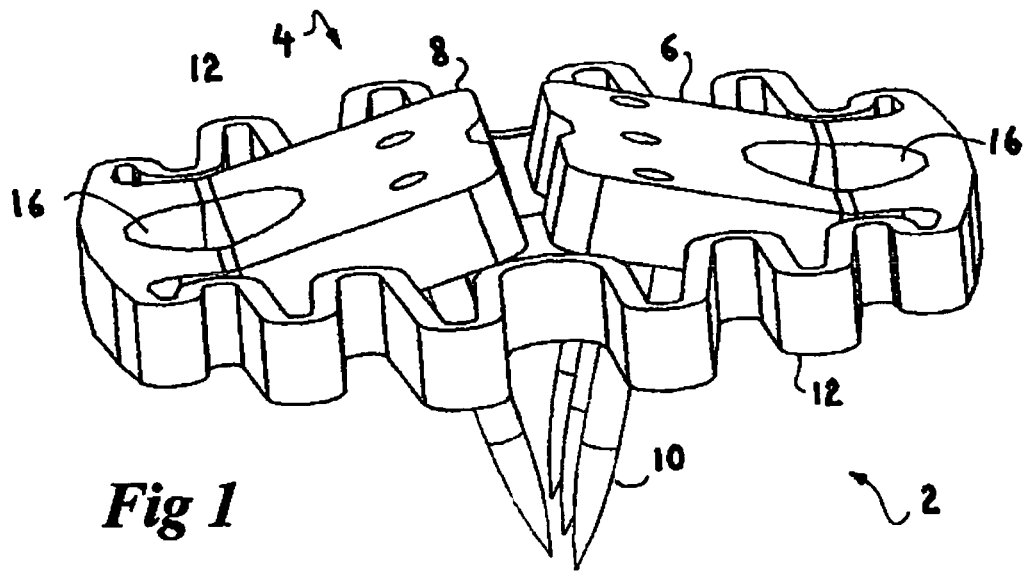
FIG. 1 is perspective view of a surgical staple used in the combined device according to the invention, highly enlarged, in closed position.
Figure 2:
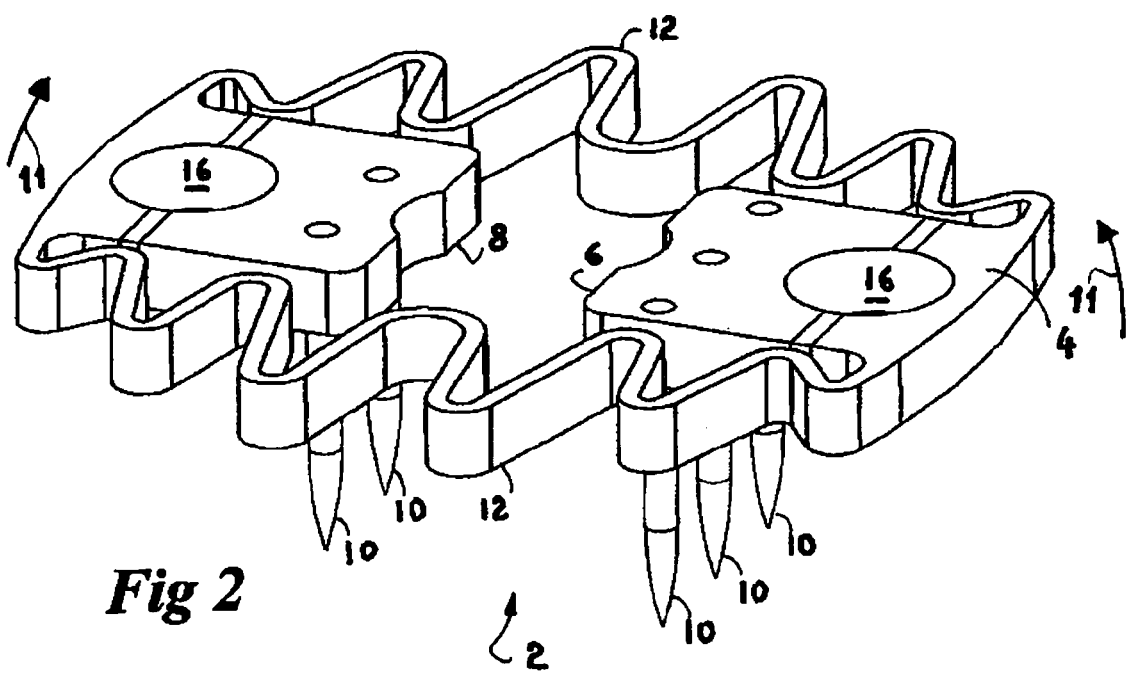
FIG. 2 is a perspective view of the staple of FIG. 1 in open position.

FIGS. 1 and 2 show, highly enlarged, a staple 2 according to the invention. To give a rough idea, the thickness of the back 4 of the staple 2 shown is about one millimeter and the length of the pins around 4 mm. The back 4 comprises two parts 6, 8 that can move relative to each other, each supporting a row of pins 10. These pins lie substantially along an axis perpendicular to the plane of each of these parts 6, 8 of the back 4. They are preferably arranged in a staggered fashion so as to ensure uniform tissue clamping.

The staple may be made either of a springy (generally metallic) material, as for example Nitinol, or of a plastically deformable material.

In the case of a springy material, in the absence of external stresses, shown in FIG. 1, the axes of the pins 10 of the two rows converge, making an angle of about 30 to 40°. This is an important point since, as will be seen later, it allows the lips of a wound to be closed up without disturbing the relative positions of the various layers of a wall of an organ.

Figure 3:
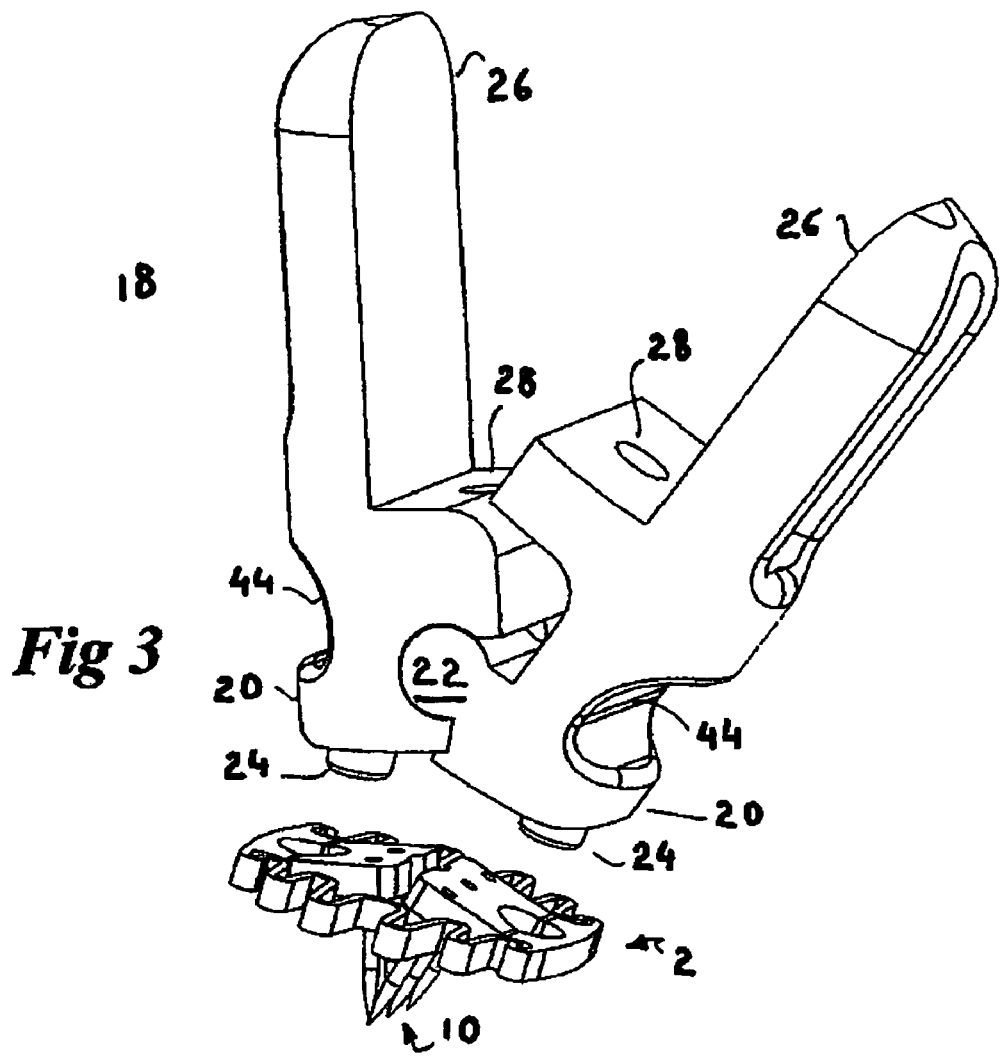

When a torsion 11 is applied to the back 4 (see FIG. 2), the axes of the two rows of pins 10 become aligned parallel to an axis substantially perpendicular to the general plane of the back 4. In this configuration, the staple offers minimal resistance to penetration into the the tissues. The two parts 6, 8 of the back 4 of the staple are joined together by zig-zagged springy joins 12, thereby making it possible, apart from aligning the pins, to move the two parts 6, 8 away from each other. The two parts 6, 8 of the back 4 are separated by a central opening 9 that allows a puncturing needle 14, which will be described in detail later, to be inserted through the back 4 and through the two rows of pins 10. Two orifices 16 made in the two parts 6, 8 serve as means for grasping the staple 2. Their usefulness will become apparent with reference to FIGS. 3 and 4.

Figure 4:
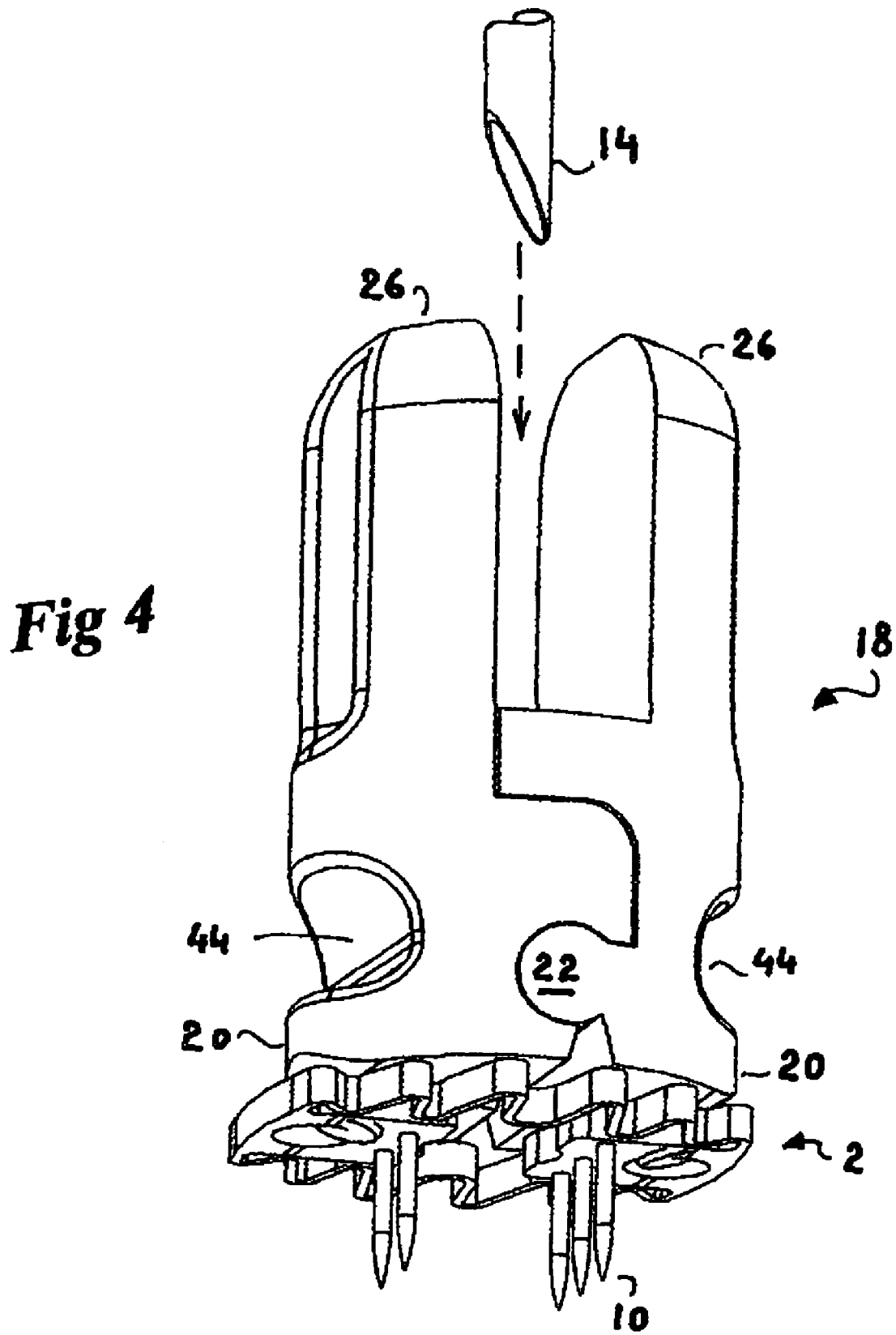

FIG. 3 shows, again in the case of a staple with an elastic back, a clamp 18 provided with two jaws 20 that can pivot relative to a common axis 22. Each of the jaws 20 is provided with a gripping stud 24 for cooperating with the orifices 16 in order to grasp the staple 2. When the clamp is in the open position, the studs 24 are aligned so as to allow easy engagement and disengagement of staple 2. By bringing the two handles 26 of the clamp 18 together (which can be performed manually just before a surgical operation), a pulling force is exerted on the jaws 20 which, via the studs 24, brings the staple 2 into its stressed position, in which the two rows of pins 10 have parallel axes and in which the central opening 9 is distended. When the clamp 18 is in the closed position (as shown in FIG. 4), the distended zigzag joins 12 of the staple 2 exert a force on the jaws 20 tending to re-open them. Their retention in the closed position, and consequently the securing of the staple 2 to the clamp 18, is provided by a locking mechanism. It is the puncturing needle 14 itself, inserted through two holes 28 passing through the handles 26 of the jaws, which in this case provides this locking mechanism.

If a staple with a plastically deformable back is used, a clamp 18 of slightly different configuration will be used, as shown later.

Figure 5:
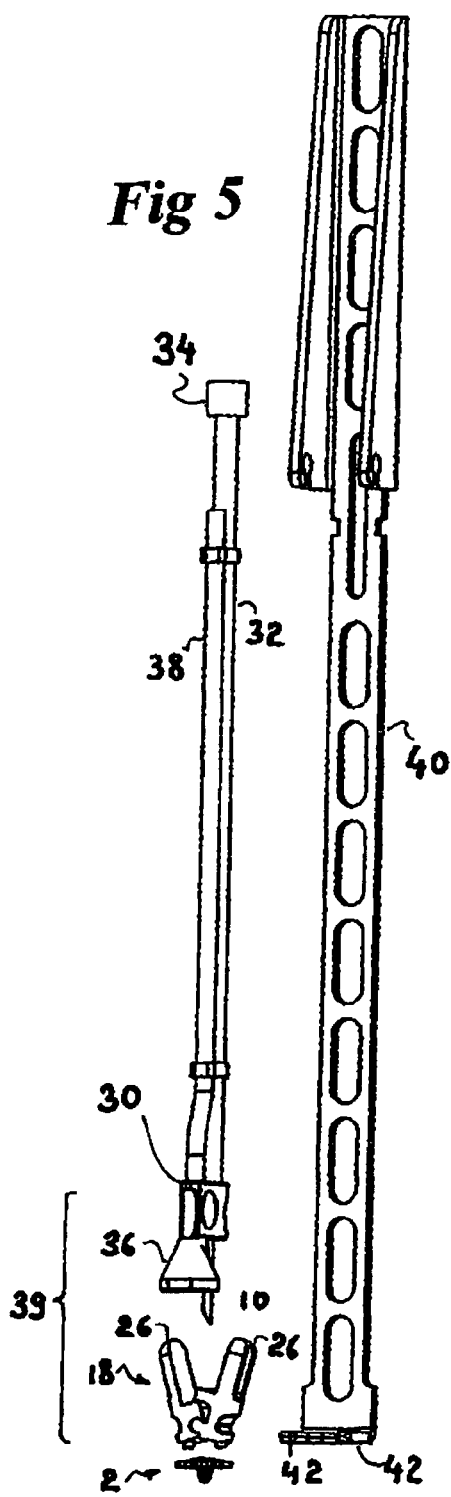
Figure 6:
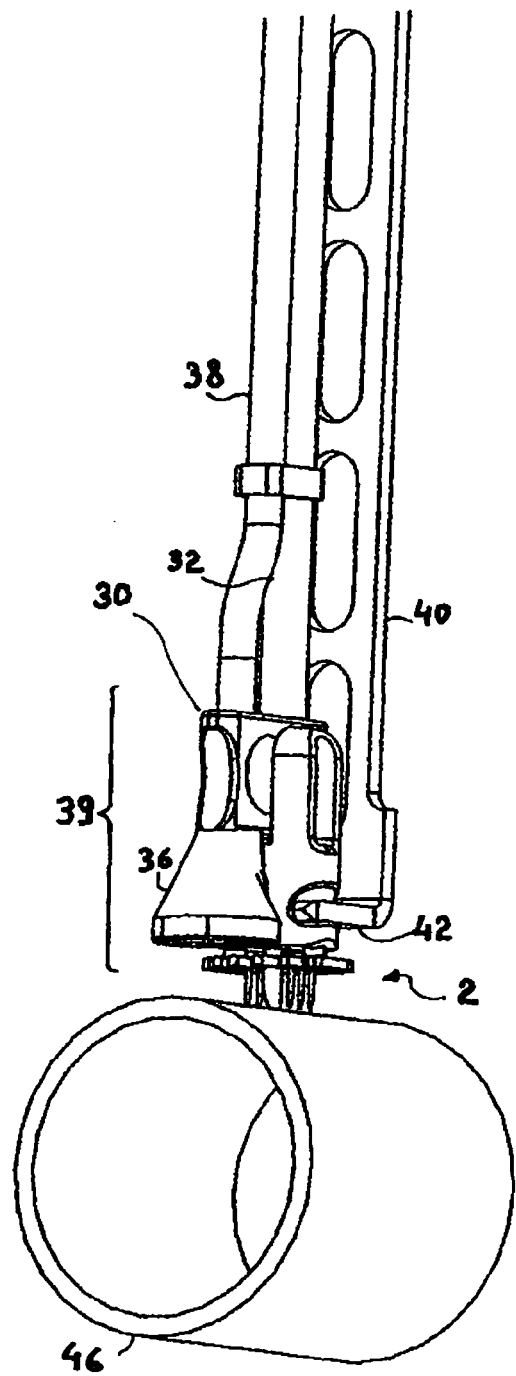

FIGS. 5 and 6 show, in exploded view and after assembly respectively, the various elements of the combined puncturing device of the invention.

The puncturing needle 14 is inserted into a support 30 which is connected to a conduit 32, the proximal end of which is provided with a connector 34 for connection to a source of fluid such as, for example, a cardioplegia solution. It may be seen that the needle support 30 supports a particular member laterally, namely a sucker 36 connected via a second conduit 38 (running parallel to the conduit 32) to a vacuum pump.

The clamp 18, the needle 14, its support 30 and the sucker 36 together form the "head" 39 of the combined puncturing device of the invention. This head 39 is supported by an introducer 40, which is terminated here by a "fork", i.e. two tips 42 that project from its distal end and that, when inserted on either side of the clamp 18 into grooves 44 provided for this purpose, allow the head 39 to be manipulated without the pivoting of the jaws of the clamp 18 being impeded.

The succession of FIGS. 6, 7, 8 and 9 fully explain both the operating method and the advantages of the device of the invention.

In FIG. 6, the elastically deformable staple 2 has been mounted on the clamp 18 and the latter is kept closed by the needle 14. The head 39 of the device supporting the staple 2 is then inserted into the introducer 40. The device is introduced into the thoracic cage of a patient and the head 39 is applied to the wall 46 of a blood vessel or of a hollow organ to be punctured (for example, the aorta). Since the material of the introducer 40 is ductile, the operator has the ability to bend it if the wall 46 of the vessel is not at the right angle. He firmly sinks the pins 10 of the staple 2 into the wall 46, their axes lying at that moment parallel to the axis of the needle 14 and/or the needle 14 itself (as will be seen later, it is not essential for the needle 14 to be inserted at the same time as the pins 10 of the staple 2). The dimensions of the pins 10 have been designed according to the thickness of the wall to be penetrated, namely a length long enough to ensure firm anchoring and an optimum diameter in order to prevent tearing of the tissues when the staple 2 is closed up.

The operator then fixes the head of the device against the wall. In this case, he applies vacuum to the sucker 36, which consequently presses the head 39 firmly against the wall 46 of the vessel and keeps it in place thereon. The operator can then disengage the head 39 of the introducer 40, by moving it translationally sideways, releasing the tips 42 of the "fork". Since the conduits 32 and 38 are flexible, the operator can move them away from the operating area and continue the operation in progress without further worrying about them.

It should be noted that the sucker 36 is not the only device that can be used to immobilize the device against the wall of the artery—it is also possible to use a clamp or a lasso loop surrounding the perimeter of the artery.

Figure 7:
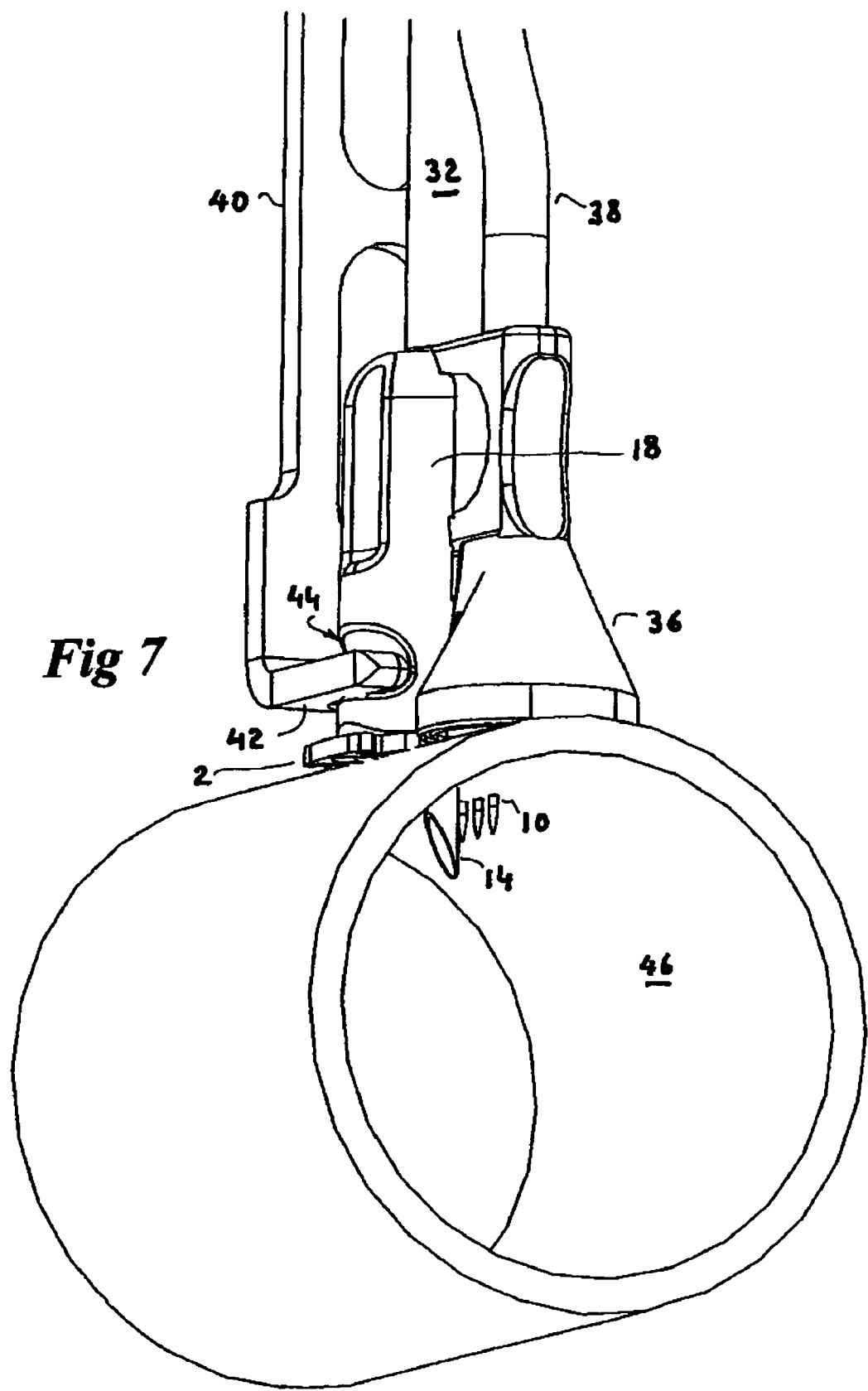

The situation is now at the stage shown in FIG. 7. Either blood can be removed from the aorta or, on the contrary, a product of some kind can be injected thereinto, via the conduit 32 and the hollow needle 14.

Figure 8:
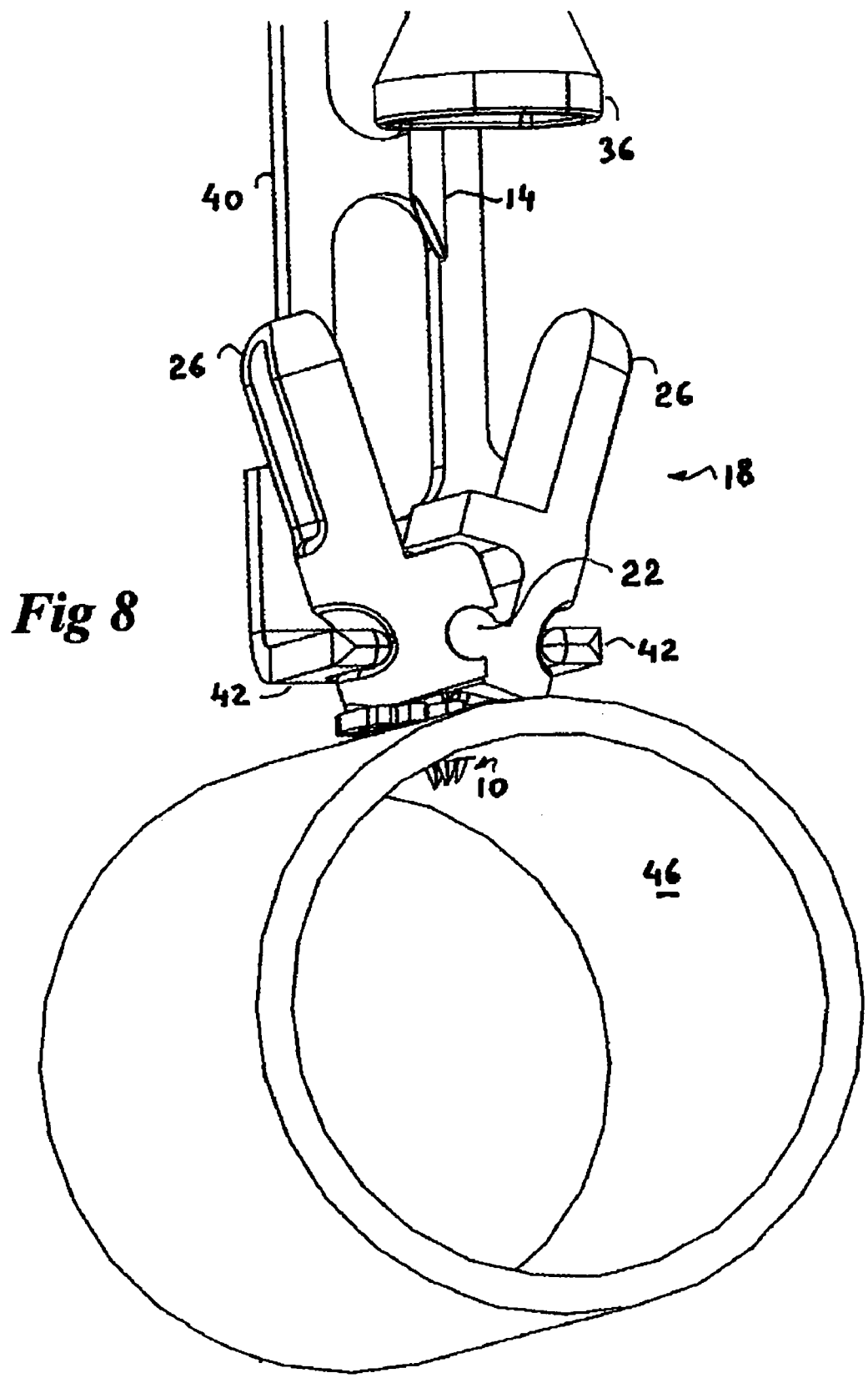

In FIG. 8, the operation is in the terminal phase: it is no longer necessary, at this moment, to keep the perfusion needle 14 in place. The operator refits the introducer 40, by inserting the tips 42 of the "fork" into the grooves 44 of the clamp 18. He grasps the proximal end 34 of the conduits 32, 38 using a device (not shown), possibly attached to the introducer 40, releases the vacuum on the sucker 36 and pulls on the support 30.

As the needle 14 comes out, it unlocks the clamp 18 and releases the staple 2. If this is a springy staple, the two rows of pins 10 of the staple 2 come together and/or converge through the action of the zigzag joins 12, causing the lips of the incision caused by the needle 14 to be firmly pressed against one another and preventing any blood spilling into the operating area. This closing-up movement is supplemented, if necessary, by the axes of the pins 10 converging, this having the effect of retaining the staple 2 in the implanted position.

If a staple 2 with a plastically deformable back 4 is used, it obviously does not exert a spring effect on the clamp 18. Instead the staple 2 is fitted by pushing on the branches of the clamp, either manually or through the agency of a mechanical, pneumatic or electrical stressing means (not shown).

Next, the clamp 18 is removed, as shown in FIG. 9. The staple 2, made of a biocompatible material well tolerated by the body, remains in place. Given its geometry, if necessary it can even be removed without any problem during a subsequent operation.

FIG. 10 shows another embodiment of the device of the invention. In this embodiment, the needle 14 is replaced with a hollow cannula 48 through which the operator introduces a trocar 50, so as to make a neater (straight) incision and one that is better centred with respect to the rows of pins 10 of the staple 2 into the wall 46. The cannula has the advantage of allowing an optimum flow rate of the fluid that passes through it. Of course, it is possible to use the trocar 50 only if the introducer is straight or substantially straight. Moreover, if a conventional puncturing needly is used, the relative position of the stud 24 or of the jaws 20 of the clamp 18 may be offset with respect to the axis of the needle 14 in order to centre the incision better.

Figure 11:
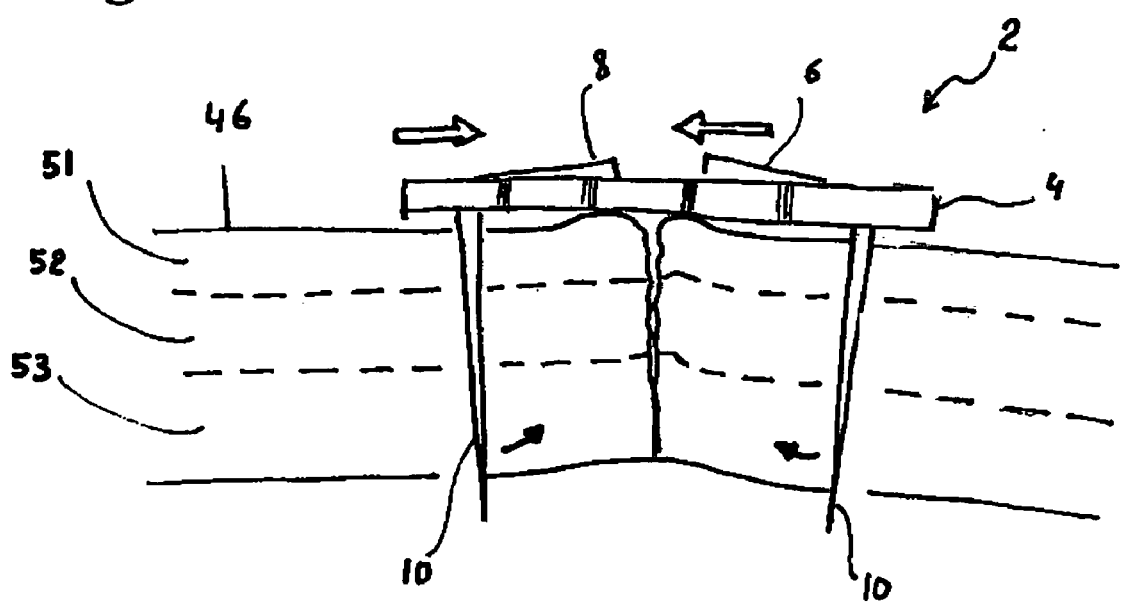
FIG. 11 is a schematic sectional view of the staple in operation.

FIG. 11 shows in greater detail the action of the staple 2 on the tissues. As may be seen, the various layers (the outer layer 51, the tunica media vasorum 52 and the outer and inner layers of the tunica intima vasorum 53, etc.) of the wall are held in place practically without any deformation relative to their initial position, which promotes problem-free cicatrization. As may be seen, the pins 10 have a length, relative to the thickness of the tissues penetrated, that is sufficient to allow deep anchoring. It is not compulsory that, as represented, they go right through the wall. The pins may if required be provided with barbs (not shown). In a general way, one ensures that the pins 10 are not too long and that they will thus not penetrate the opposite side of the punctured organ; their actual length (equal, shorter or longer than the thickness of the wall to penetrate) is determinated according to the nature of the organ itself and the physiological properties of the wall.

It should be understood that the staple 2, although shown here with two rows of a limited number of pins 10 (two and three, in this case), may comprise a different number of pins (from 2 to N pins) depending on the characteristics of the wound to be closed. It is advantageous for the pins 10 of the two rows to be arranged in a staggered fashion, as shown, so as to close the wound over its entire length. Although the present device has been shown here within the context of a mini-invasive surgical operation, it may also be used in standard surgery.

Moreover, if it is desired to use the device only in its wound-closing function, the needle 14 is replaced with a simple end-fitting that does not extend beyond the jaws of the clamp.

FIG. 12 shows another embodiment of the head 39 of the device, suitable for using a staple with a plastically deformable back. In this case, the clamp 18 is provided with a bracelet acting as a locking means, which, in the absence of any stress, keeps the studs 24 of the clamp in a position such that the staple 2 can be fitted thereonto in the open state (i.e. with the pins 10 in a substantially parallel position). The support of the needle 14 comprises a core 56 forming a cam, while the internal faces of the handles 26 of the clamp 18 each comprise a ramp 58 capable of cooperating with the external faces of the cam-forming core 56.

The device in the process of puncturing is shown in FIG. 13. When the puncturing operation has been completed, the operator exerts a relative pulling force on the needle 14, the head of the device also being held firmly against the wall (see FIG. 14). As in the case of the other version of the device, this pulling force is exerted either manually (via a lever system for example) or pneumatically or even electrically.

During the transition, the core 56, acting as a cam, forces the handles 26 of the clamp 18 to move apart, thus tightening the jaws 20 and consequently closing the staple 2, which constricts the punctured tissue.

Figure 15A:
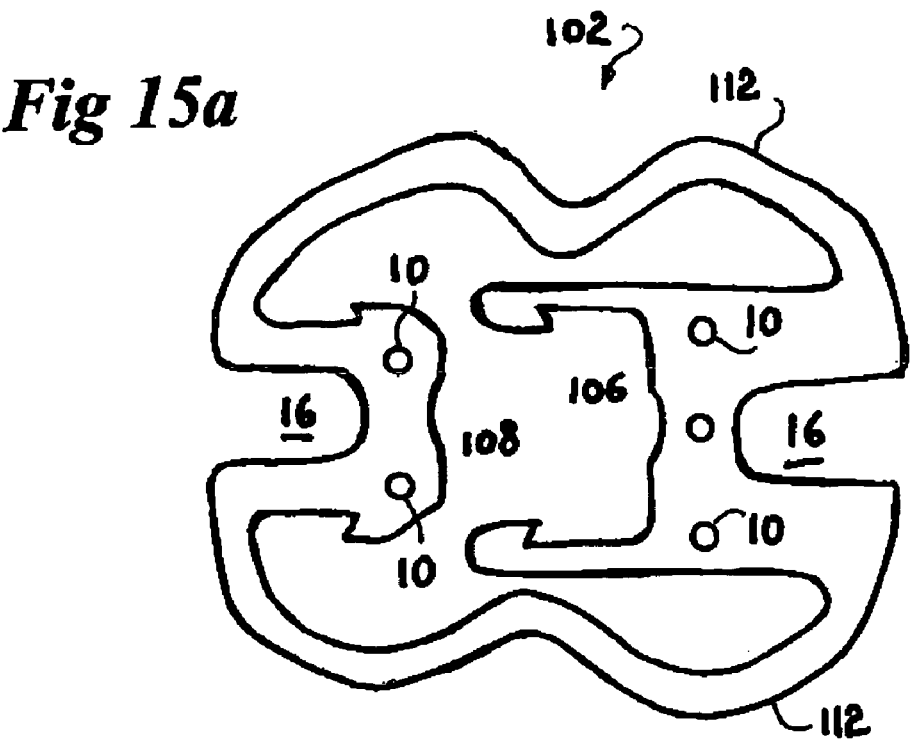
FIGS. 15a to 15c are plan and elevation views of another embodiment of a plastically deformable staple.
Figure 15B:
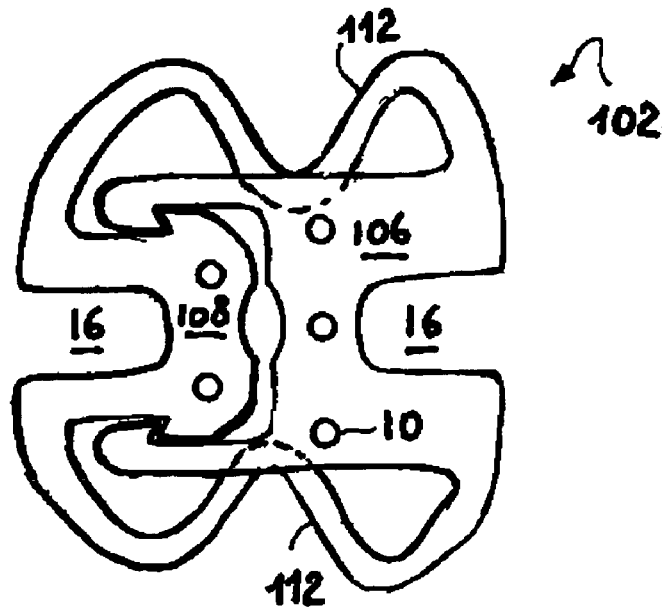
Figure 15C:
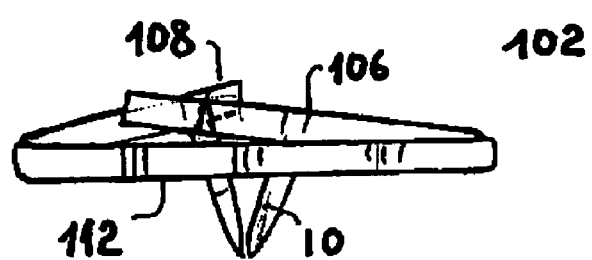
Figure 16:
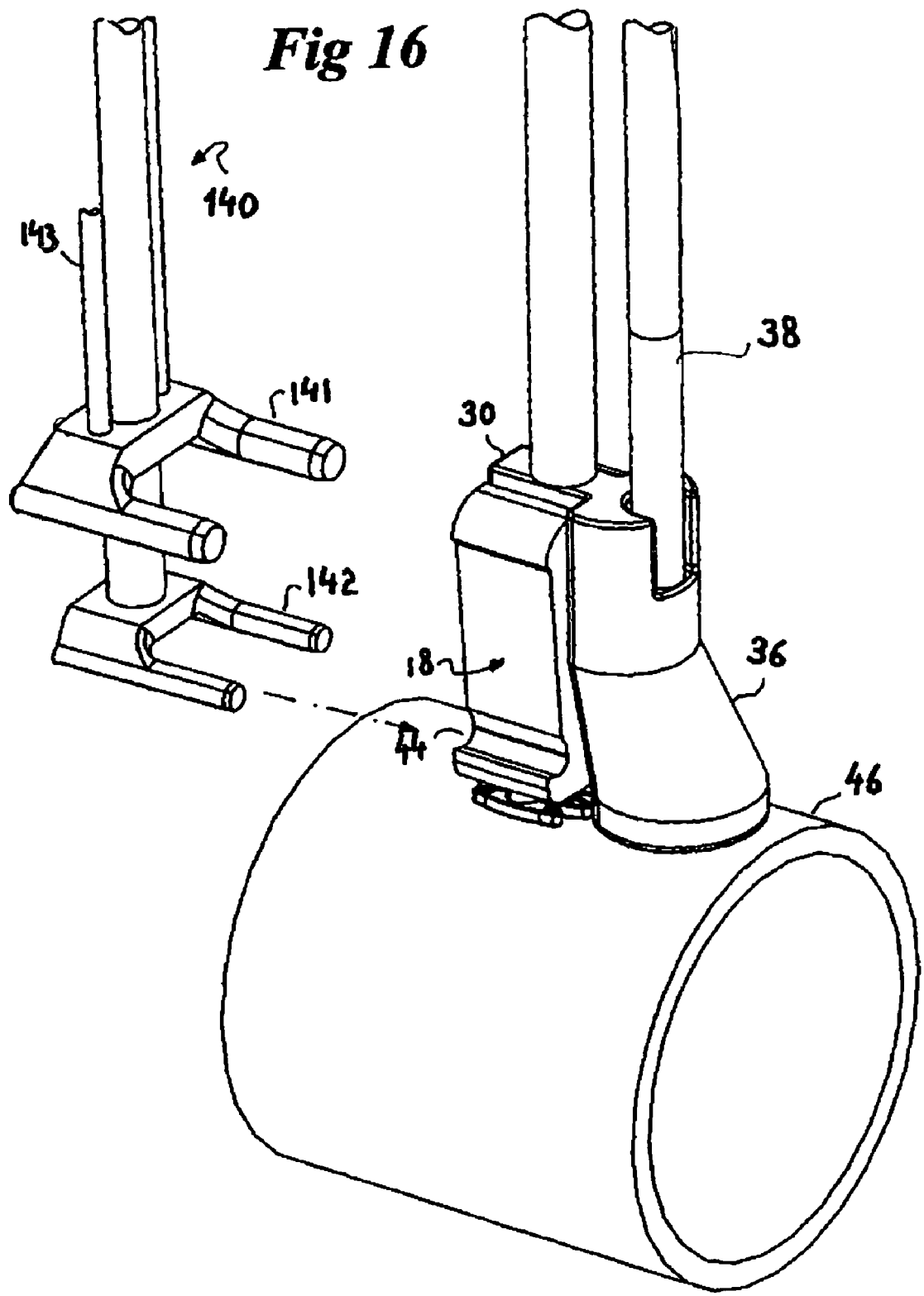
FIGS. 16 to 19 are perspective views of another embodiment of the introducer and of the placement device of the staple.
Figure 17:
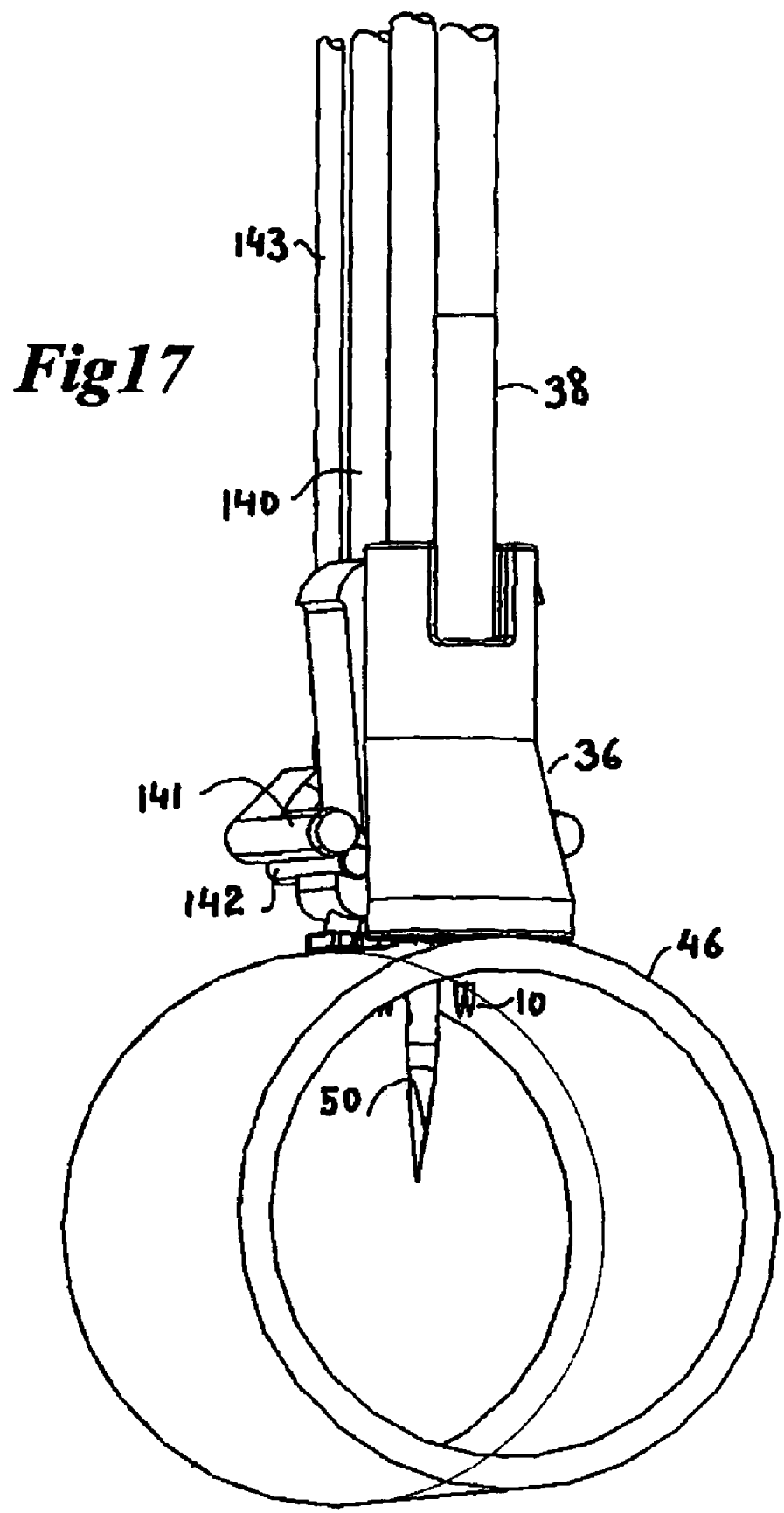
Figure 18:
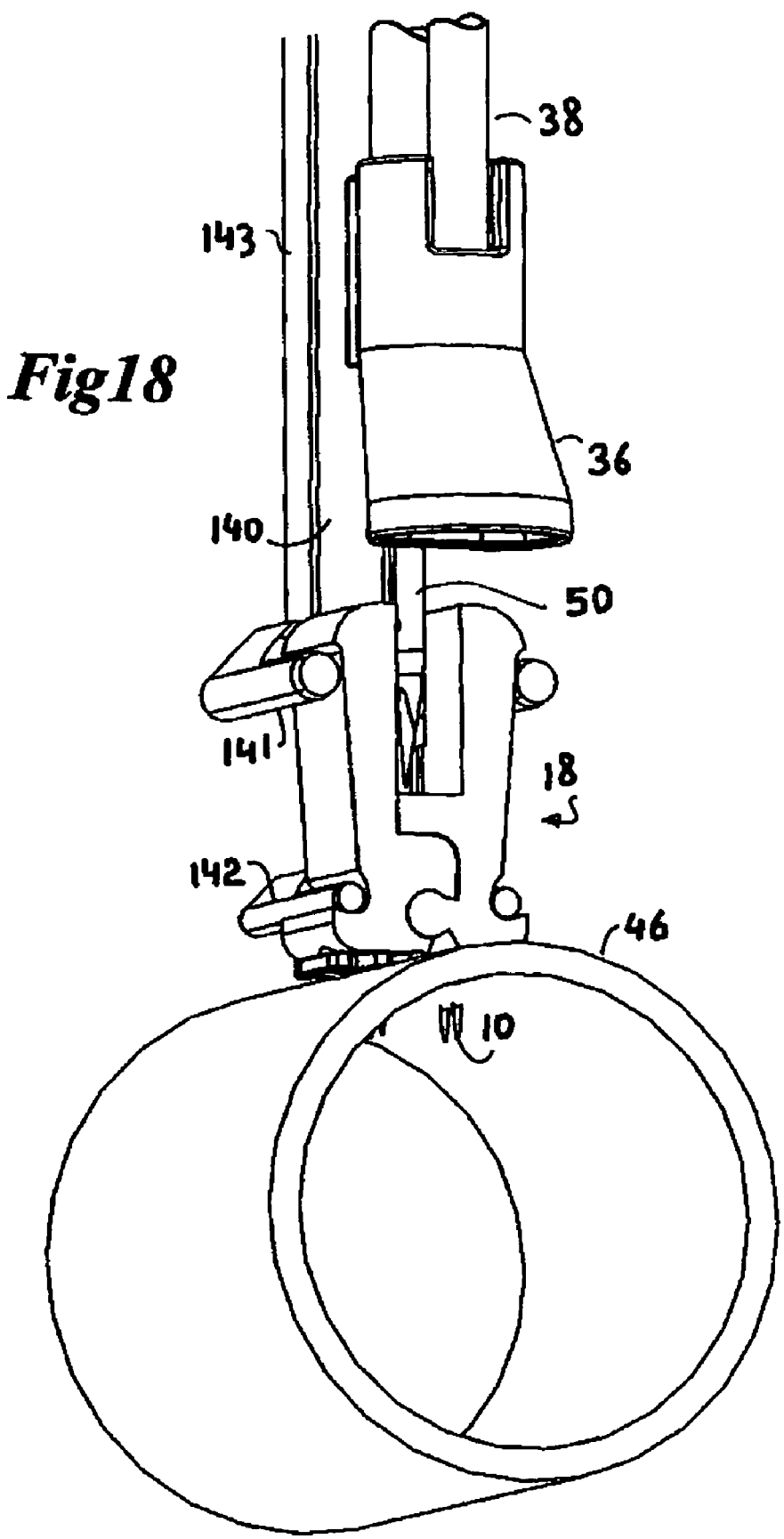

FIGS. 15a to 15c display another embodiment of the staple 102, in this case a plastically deformable staple. As in staple 2, staple 102 comprises joins 112. When being bent by clamp 18, the joints 112 urge the axes of the pins 10 fitted on the parts 106, 108 of the back to converge. Hooks 113, 115 interlock, forbidding the staple to open once it has been closed on a wound.

FIGS. 16 to 19 display another embodiment of introducer 140. This introducer is fitted, besides the already described "fork" 142, with a movable "fork" 141. The role of this fork is to make easier the removal of the puncturing needle 14.

Figure 19:
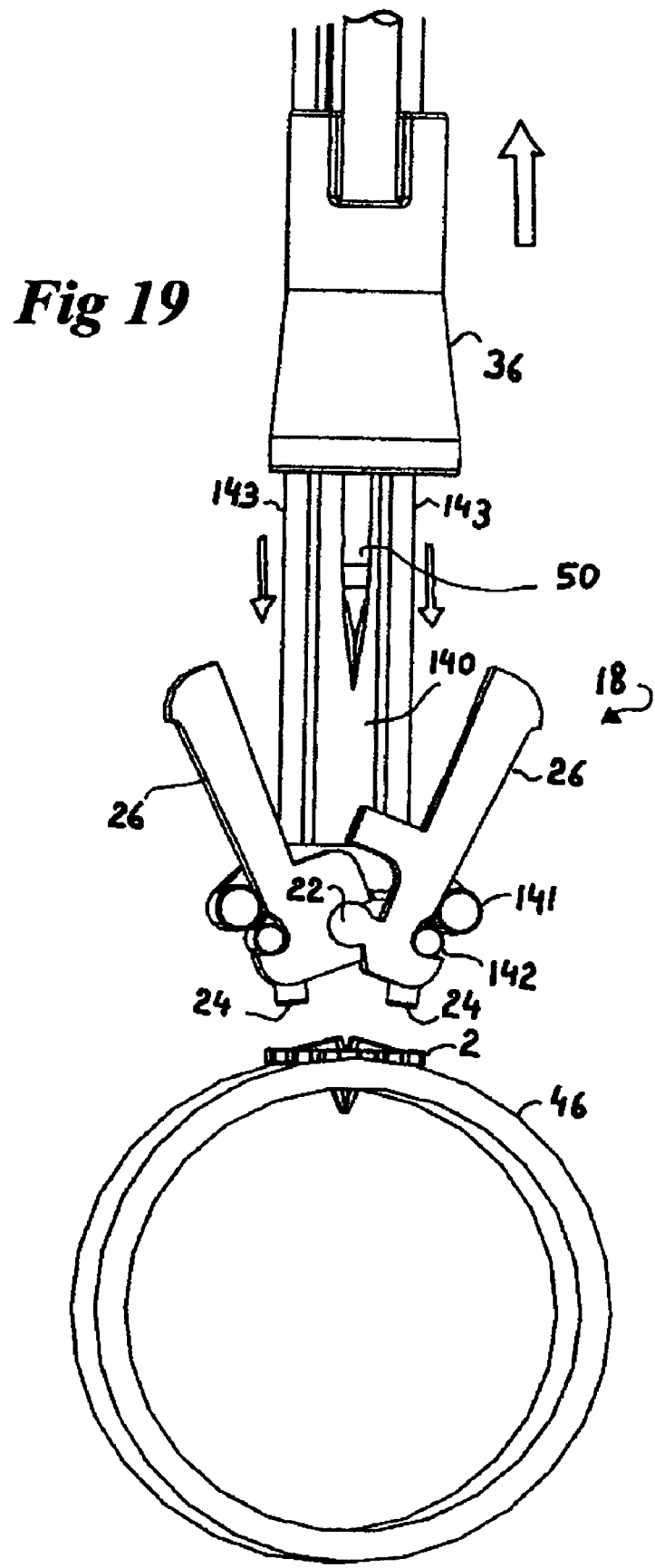

As needle 14 locks the jaws of the clamp 18, it is submitted, at the moment of the removal, to a non-neglectible friction resistance. To prevent that the operator would have to exert a too high traction force on the needle at the moment of the removal—implying a risk to make a mistake—a means to slightly close the handles 26 of the clamp 14 is provided, which nullifies the friction on the needle 14. At FIG. 16, the introducer 140 (that was removed during the operation to free the operating field) is put in place again on the head of the device by the operator. At FIG. 17, the tips 142 of the fork are sled into the grooves 44 of the clamp 18, the movable fork 141 being maintained close to the fixed fork 142 via control rods 143. The movable fork 141 is then sled towards the proximal side of the device by the operator, causing the handles of the clamp 18 to be temporarily held in closed position. The needle may then be removed without effort (see FIG. 18). The operator then pushes the movable fork towards the distal end of the device, freeing the clamp 18 and provoking the closing of the staple 2 (FIG. 19).

Figure 20:
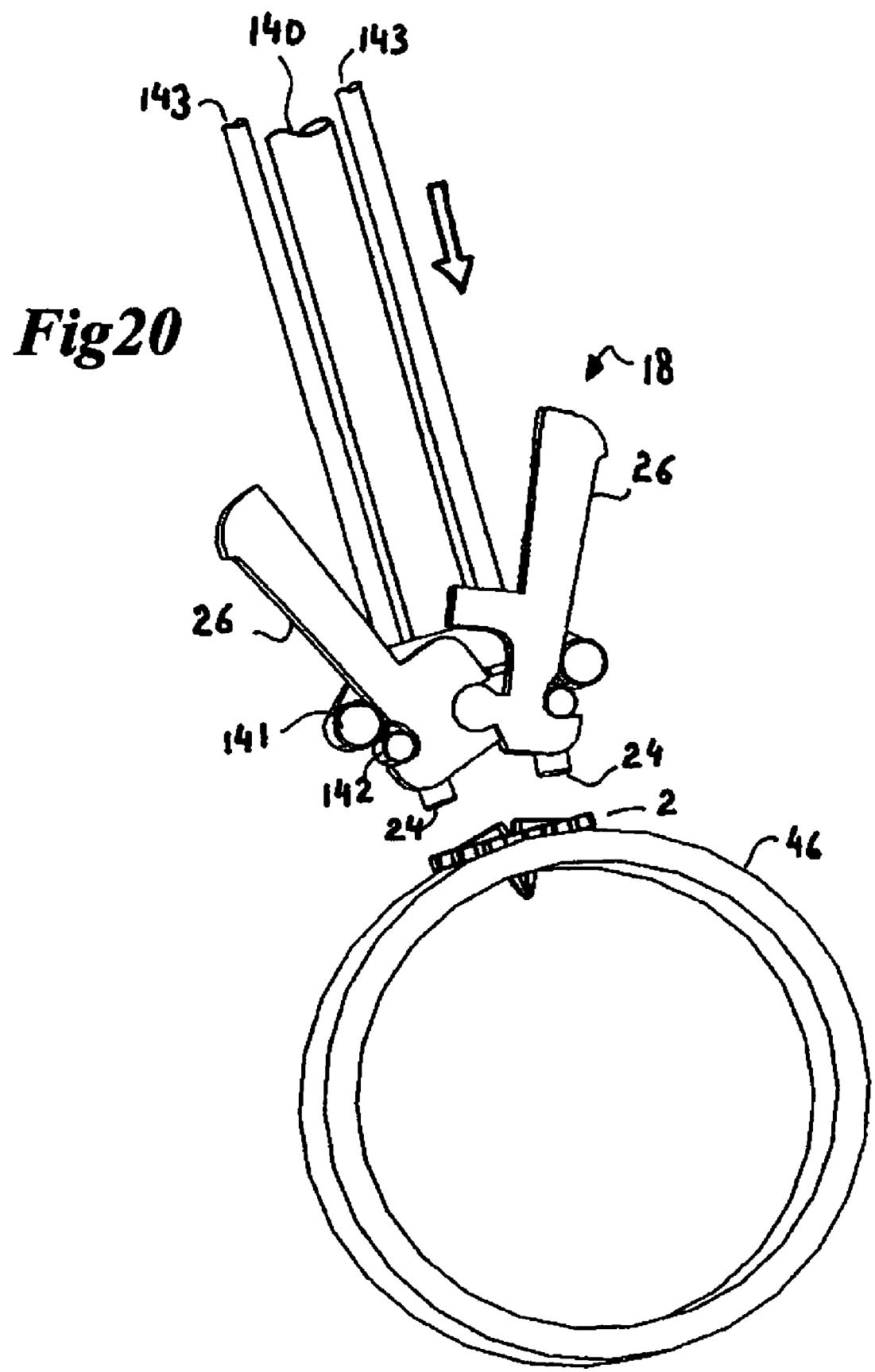
FIGS. 20 and 21 are perspective views showing the removal of a staple.
Figure 21:
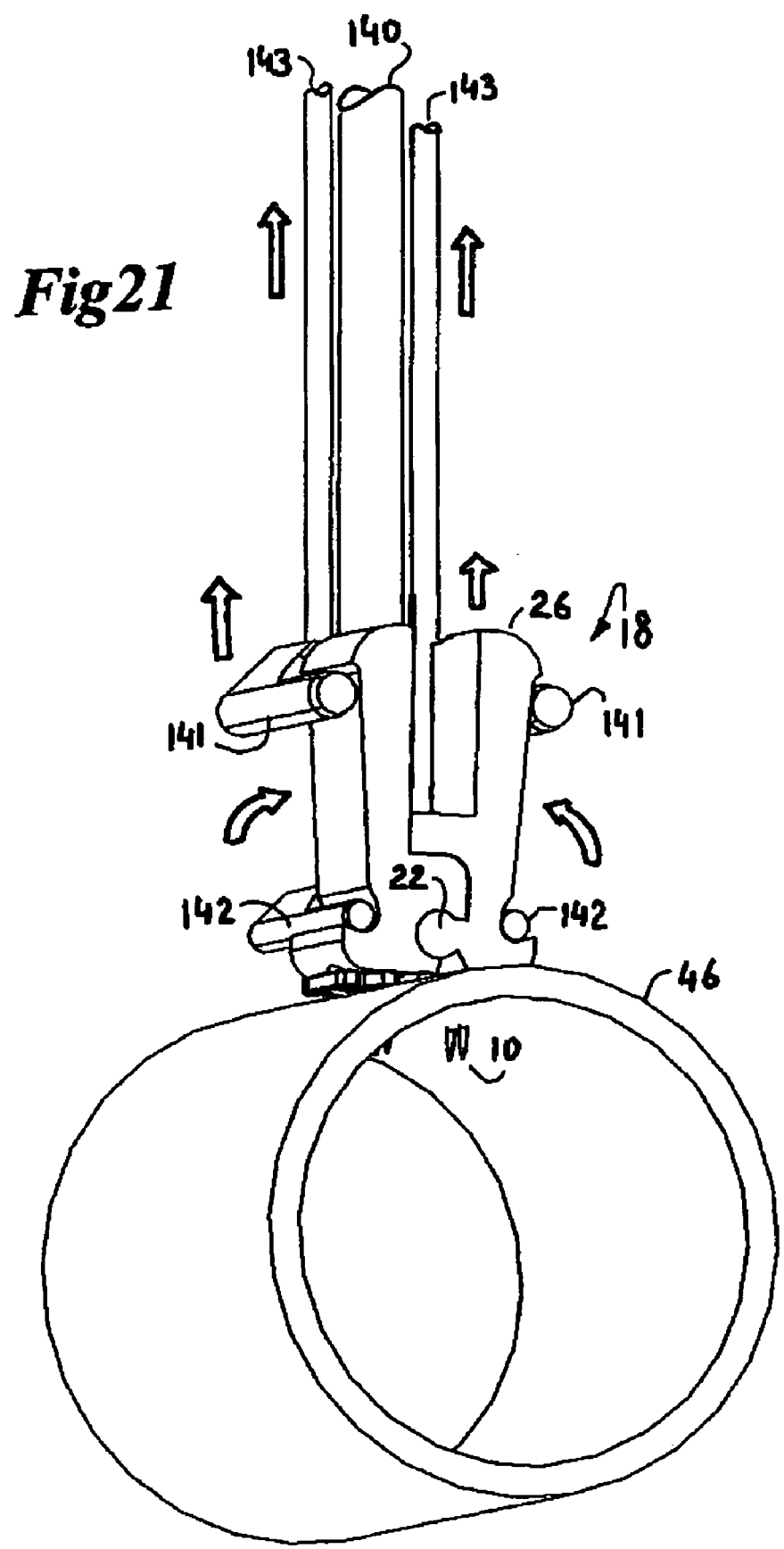

One advantage of introducer 140 is that it allows a possible removal of the staple 2, either in the case of mistake during the operation, or during a possible further operation. As disclosed at FIGS. 20 and 21, to remove an already placed staple, it suffices to use a clamp 19 inserted on an introducer 140 to be able to grasp this staple again: the gripping studs 24 having been inserted into the orifices 16 of staple 2, the movable fork is pulled backwards; clamp 19 closes, bringing the pins 10 back in parallel plans. Staple 2 is then pulled out without problem.

FIGS. 22 to 29 display another embodiment of the device of the invention.

Though the whole elements are similar to what was described above, this embodiment is more complete and still reduces possible mistakes.

FIG. 22 displays an exploded view of the various elements of this embodiment. The most distinctive element is the presence of a sucker 236 made integral with support 230 and which encloses the clamp and the puncturing system.

Another distinctive element is the fact that the role of the introducer (40, 140) is ensured partially by the shaft 260 of a trocar 250 and partially by a pusher 262, as explained hereinbelow.

Figure 23:
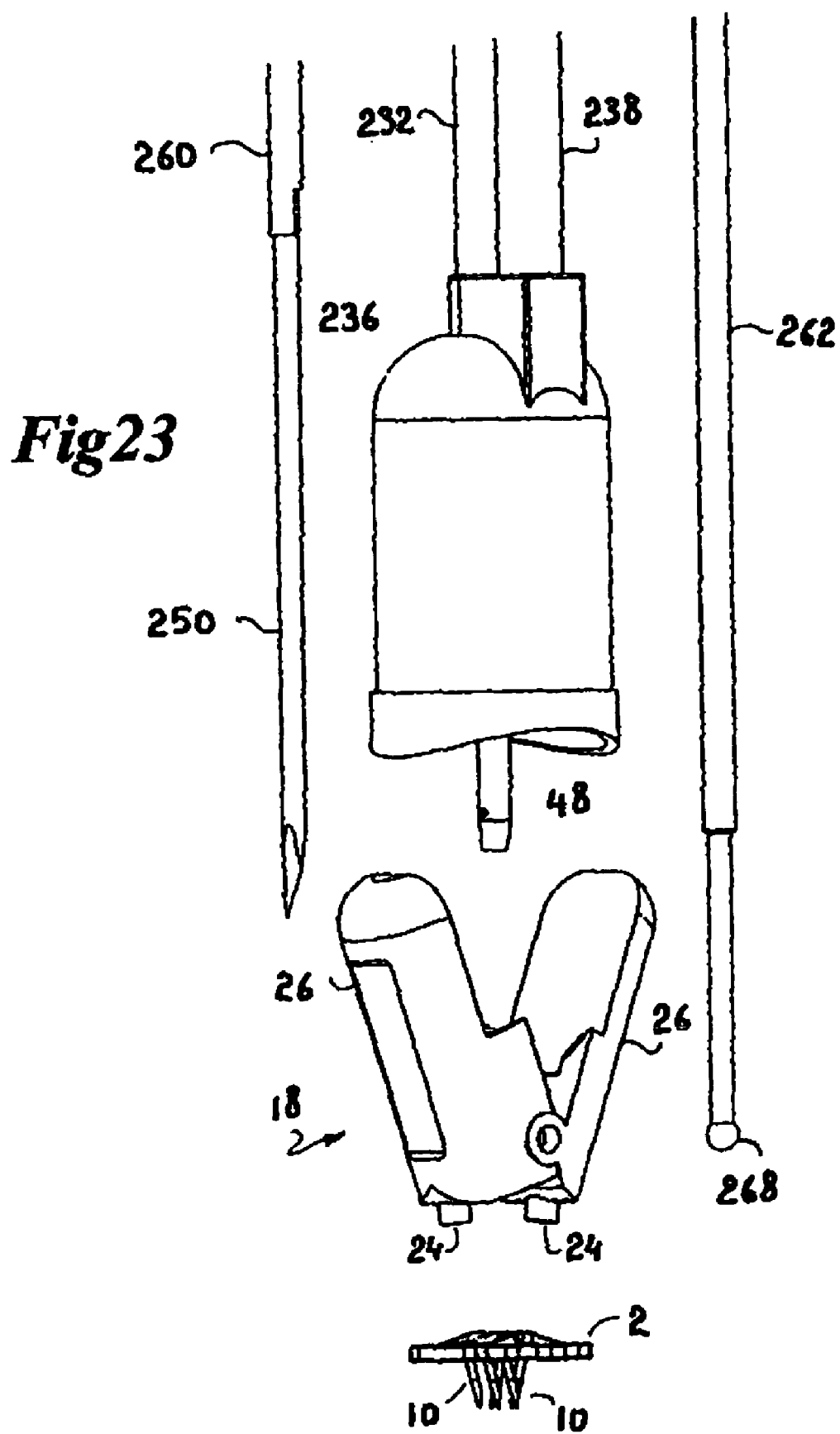

The head 239 of the device is shown in a more detailed manner at FIG. 23. As in the former embodiments, this head 239 is connected to the proximal part of the device by a first conduit 232 for the passage of fluid, the latter opening onto the cannula 48, and by a second conduit 238 for ensuring vacuum in the sucker 236.

When introducing the head 239 into the body of the patient, it suffices (as shown at FIG. 26) to slide the trocar 250 and its rigid shaft 260 into the first conduit 232 to obtain a device which is perfectly rigid in its medium part, which allows to neglect the use an introducer 40, 140 as described above. During the removal of the device, the pusher 262 will play a similar role, as shown hereinbelow.

FIG. 23 to 27 show the various steps for introducing the puncturing device: the clamp being in open position, the gripping studs 24 of the clamp are moved towards each other, bringing the staple in insertion position, i.e. with the axes of the two rows of pins 10 essentially parallel to each other (see FIG. 24); the shaft 260 of the trocar is sled into the conduit 232 and the clamp holding the staple is brought into the bell-shaped sucker 236 (see FIG. 25). The locking of the clamp is assured here by the internal wall of the bell 236, which maintains the clamp via a contact with the tip of the handles 26. The operator, handling the rigidified device by its proximal end, introduces the head into the body of the patient up to the wall 46 of the organ to be treated, pierces this wall with the trocar 250, while the pins 10 run trough the wall 46. Vacuum is established in the bell-shaped sucker 236, thus urging the head of the device against the wall 46. The trocar 250 and its rigid shaft 260 are then removed.

FIG. 17a displays a sectional view of the various elements of the head 239 of the placed device.

The mouth 264 of the sucker, substantially saddle-form, fits perfectly to the curve of the wall 46. The hollow cannula 48 goes through the wall 46. A possible loss of fluid provoked by the incision is balanced by the sucking through the vacuum conduit 238. The profile of the inner wall of the sucker is designed so as to maintain the clamp in closed position, and, accordingly, the staple remains in open position.

One advantage of this embodiment is that the traction exerted on the wall 46 is not off-centred with respect to the solicitations exerted on the cannula 48, as in the case shown at FIG. 10, which reduces the possibilities of unexpectedly tearing the device away during the operation.

Figure 27B:
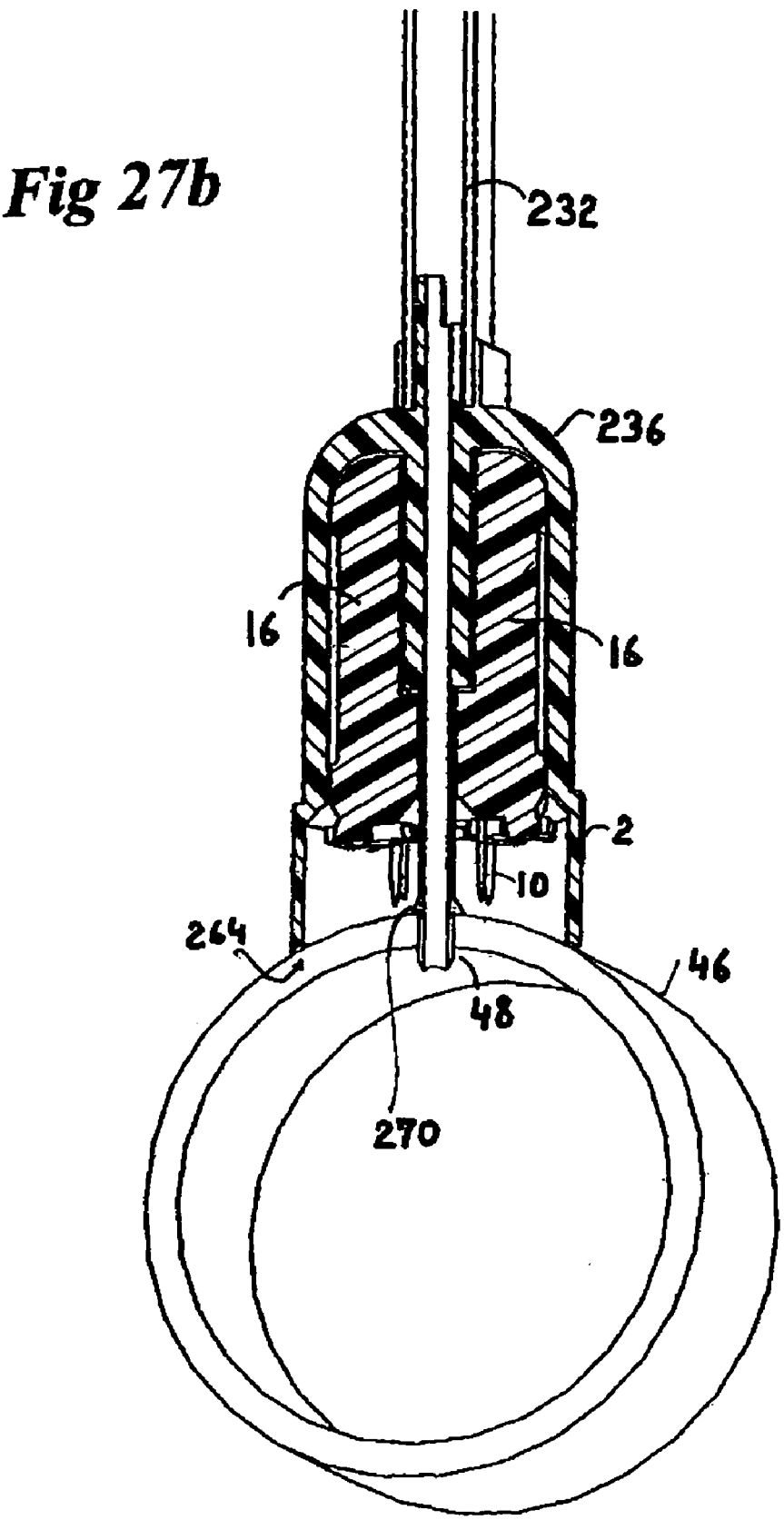
FIG. 27b is a sectional view of another embodiment of the device of FIG. 22.

FIG. 27b shows another possible embodiment: the mouth 264 of the sucker 236 is here somewhat longer than what is displayed at FIG. 27a, so that the wall 46 is pierced only by the trocar 250 and the cannula 48. It is merely at the very moment of the removal that the staple 2 comes in contact with the wall 46 and that the pins pierce said wall. To prevent an untimely bending of the wall provoked by the sucking, a stopping ring 270 is fitted on the cannula 48.

Figure 28:
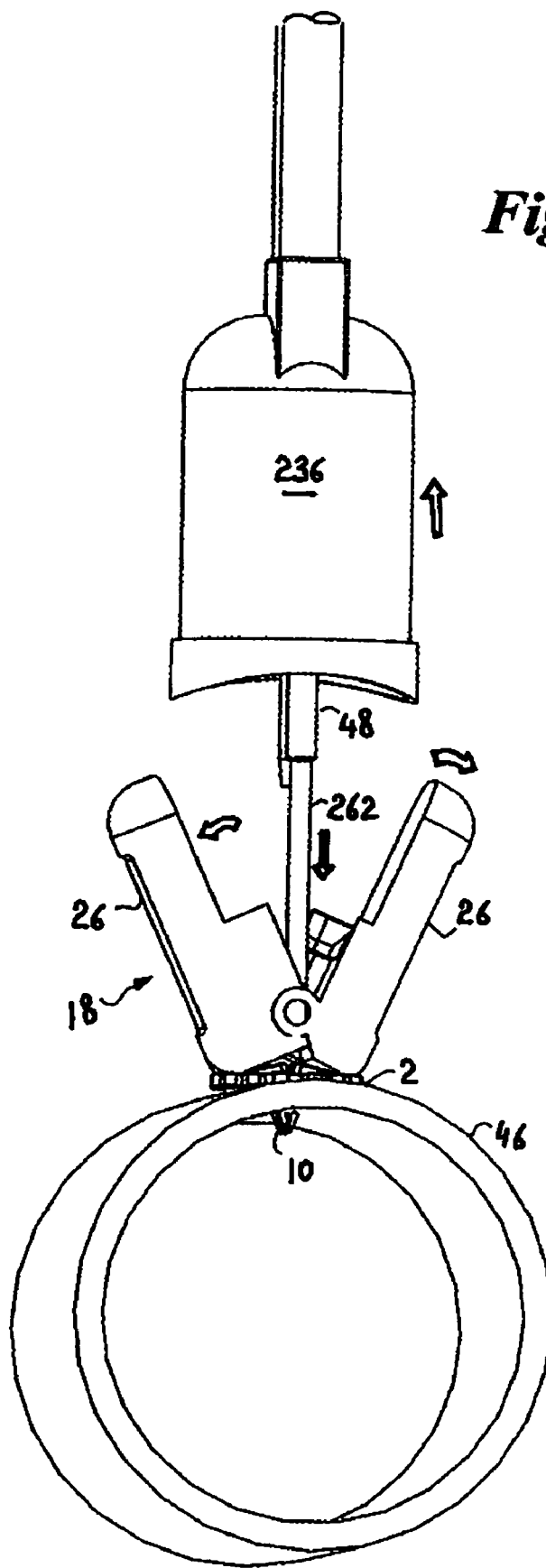

FIGS. 28 and 29 show the removal step of the puncturing device and the occlusion of the punctured orifice: the operator introduces, from the proximal side of the device, le pusher 262 into the vacuum conduit 268 of the sucker 236. The vacuum is then interrupted and he pulls the proximal side of the conduit via a handle 263. The sucker goes back, while the clamp 18 is firmly maintained in place by the pusher 262. As soon as the sucker has passed the free tips of the handles 26 of the clamp 18, the latters are freed and, in the case of a resilient staple, said staple takes its closed form, the tips of the pins come close to each other closing the lips of the incision. As explained with respect to the introducer 40, the shaft of the trocar 260 and the pusher 262 are bendable so that the head of the device may be brought normal to the wall 46, whatsoever the position of the organ to puncture.

At FIG. 29, the operator proceeds with the removal of the device. An end knob 268 of the pusher, cooperating with a (non visible) groove placed on the clamp 18, drawn the clamp out of the body.

The device may be delivered in a "kit" fashion, said kit comprising an applicator 140, which allows the possible removal of an ill-placed staple, or of a staple that has become unnecessary due to healing of the wound.

What is claimed is:

1. A combined device for plugging and fluidtight puncturing of a wall of a hollow organ, comprising a proximal and a distal part, which comprises:
    a surgical staple for the wall of the hollow organ, placed towards the distal part, said staple comprising a substantially flat back that can deform between a closed position of the staple and an open penetration position of the staple, and at least two spaced-apart pin rows extending each along an axis, a free end of the pins converging when the back is in the closed position, the axes of the pins of the two rows tending to align parallel to each other when the staple is in the open penetration position, so as to offer minimal resistance to penetration into the tissues, the back of said staple being provided with a central opening, and the back of said staple not protruding from the wall of the hollow organ when the staple is in place;
    a fluidtight puncturing system comprising a puncturing device and a hollow channel, the diameter of which corresponds to the central opening of the staple, said puncturing system being mounted on a support and connected to a fluid carrying conduit, and said puncturing device adapted to pierce the wall of the hollow organ;
    a keeping means for keeping the said staple in place, said keeping means comprising a clamp provided with two jaws and with locking means and being capable of bringing the staple from its open position to its closed position, wherein free ends of the two jaws are provided with grasping means capable of cooperating with gripping points of the staple;
    the support being connected to a traction member extending towards the distal part of the device, forming the head of the device, the surgical staple and the puncturing system being borne by the head of the device so that the penetration of the pins into the tissues and the puncturing occur simultaneously; and
    an introducer capable of introducing the head of the device inside an organism.

2. A surgical device according to claim 1, wherein the staple is elastically deformable, and the locking means are capable of keeping the staple in place on the jaws in a open position.

3. A surgical device according to claim 1, wherein the staple is plastically deformable, the jaws of the clamp being able to be actuated by a clenching means causing plastic deformation of the back of the staple.

4. A surgical device according to claim 1 wherein a tip of the puncturing device is manufactured and placed in the puncturing system in such a manner that the pins of the staple are placed on opposite sides of an incision made in the wall of a hollow organ and on a substantially symmetrical way with respect to said incision.

5. A surgical device according to claim 1 wherein a distal head of the device is detachable from the introducer.

6. A surgical device according to claim 1 wherein the closing of the staple is actuated by the removal of the support.

7. A surgical device according to claim 1 wherein the introducer includes, at its proximal side, a member for unlocking the clamp, so releasing the staple.

8. A surgical device according to claim 1 wherein the support includes retention means that can be applied against the wall of a hollow organ and can keep the head of the device in place during a puncturing operation.

9. A surgical device according to claim 8 wherein the retention means comprises a sucker, said sucker being connected to a conduit that can be connected to a source of negative pressure, and said sucker extending normal to the wall of the hollow organ and comprising a mouth adapted to be positioned adjacent to the wall of the hollow organ.

10. A surgical device according to claim 9 wherein the puncturing device and the staple retention means are placed inside the sucker.

11. A surgical device according to claim 1 wherein the introducer is plastically deformable so as to be able to present the puncturing device at right angles to a wall lying at any angle.

12. A surgical device according to claim 1 wherein the puncturing device includes a trocar that can be inserted through a hollow conduit.

* * * * *